(12) United States Patent
Jia et al.

(10) Patent No.: US 11,717,155 B2
(45) Date of Patent: Aug. 8, 2023

(54) IDENTIFYING RETINAL LAYER BOUNDARIES

(71) Applicant: Oregon Health & Science University, Portland, OR (US)

(72) Inventors: Yali Jia, Portland, OR (US); Yukun Guo, Portland, OR (US)

(73) Assignee: Oregon Health & Science University, Portland, OR (US)

( * ) Notice: Subject to any disclaimer, the term of this patent is extended or adjusted under 35 U.S.C. 154(b) by 457 days.

(21) Appl. No.: 16/998,931

(22) Filed: Aug. 20, 2020

(65) Prior Publication Data

US 2021/0052155 A1 Feb. 25, 2021

Related U.S. Application Data

(60) Provisional application No. 62/889,917, filed on Aug. 21, 2019.

(51) Int. Cl.
  *A61B 3/10* (2006.01)
  *A61B 3/12* (2006.01)
  *A61B 3/14* (2006.01)
  *G06T 7/13* (2017.01)
  *G06T 7/136* (2017.01)
  *G06T 7/12* (2017.01)

(52) U.S. Cl.
  CPC ............... *A61B 3/102* (2013.01); *A61B 3/12* (2013.01); *A61B 3/1241* (2013.01); *A61B 3/14* (2013.01); *G06T 7/12* (2017.01); *G06T 7/13* (2017.01); *G06T 7/136* (2017.01); *G06T 2207/10101* (2013.01); *G06T 2207/20072* (2013.01); *G06T 2207/30041* (2013.01)

(58) Field of Classification Search
  CPC ......... A61B 3/102; A61B 3/12; A61B 3/1225; A61B 3/1241; A61B 3/14; G06T 7/12; G06T 7/13; G06T 7/136; G06T 7/162; G06T 2207/10101; G06T 2207/20072; G06T 2207/30041
  See application file for complete search history.

(56) References Cited

PUBLICATIONS

Antony, et al., "Automated 3-D method for the correction of axial artifacts in spectral-domain optical coherence tomography images," Biomedical Optics Express, vol. 2, No. 8, Aug. 2011, pp. 2403-2416.

(Continued)

*Primary Examiner* — Jack Dinh
(74) *Attorney, Agent, or Firm* — Katherine M. Mead; Tanya M. Harding; Lee & Hayes, P.C.

(57) ABSTRACT

Methods for automatically identifying retinal boundaries from a reflectance image are disclosed. An example of the method includes identifying a reflectance image of the retina of a subject; generating a gradient map of the reflectance image, the gradient map representing dark-to-light or light-to-dark reflectance differentials between adjacent pixel pairs in the reflectance image; generating a guidance point array corresponding to a retinal layer boundary depicted in the reflectance image using the gradient map; generating multiple candidate paths estimating the retinal layer boundary in the reflectance image by performing a guided bidirectional graph search on the reflectance image using the guidance point array; and identifying the retinal layer boundary by merging two or more of the multiple candidate paths.

20 Claims, 19 Drawing Sheets
(13 of 19 Drawing Sheet(s) Filed in Color)

(56) References Cited

PUBLICATIONS

Baroni, et al., "Towards quantitative analysis of retinal features in optical coherence tomography," Medical Engineering & Physics, vol. 29, No. 4, May 2007, pp. 432-441.

Bavinger, et al., "The Effects of Diabetic Retinopathy and Pan-Retinal Photocoagulation on Photoreceptor Cell Function as Assessed by Dark Adaptometry," Investigative Ophthalmology & Visual Science, vol. 57, No. 1, Jan. 2016, pp. 208-217.

Campbell, et al., "Detailed Vascular Anatomy of the Human Retina by Projection-Resolved Optical Coherence Tomography Angiography," Scientific Reports, vol. 7, Feb. 2017, 11 pages.

Chiu, et al., "Automatic segmentation of seven retinal layers in SDOCT images congruent with expert manual segmentation," Optics Express, vol. 18, No. 18, Aug. 2010, pp. 19413-19428.

Coleman, et al., "Age-related macular degeneration," Lancet, vol. 372, No. 9652, Nov. 2008, pp. 1835-1845 (24 pgs.).

Dai and Sun, "Automated Layer Segmentation of Optical Coherence Tomography Images," 4th International Conference on Biomedical Engineering and Informatics, vol. 1, Oct. 2011, pp. 142-146.

Debuc, "A Review of Algorithms for Segmentation of Retinal Image Data Using Optical Coherence Tomography," Image Segmentation, Apr. 2011, pp. 15-54.

Early Treatment Diabetic Retinopathy Study Research Group, "Early Treatment Diabetic Retinopathy Study Design and Baseline Patient Characteristics. ETDRS Report No. 7," Ophthalmology, vol. 98, No. 5, May 1991, pp. 741-756.

Fang, et al., "Automatic segmentation of nine retinal layer boundaries in OCT images of non-exudative AMD patients using deep learning and graph search," Biomedical Optics Express, vol. 8, No. 5, May 2017, pp. 2732-2744.

Fernandez, et al., "Automated detection of retinal layer structures on optical coherence tomography images," Optics Express, vol. 13, No. 25, Dec. 2005, pp. 10200-10216.

Garvin, et al., "Automated 3-D Intraretinal Layer Segmentation of Macular Spectral-Domain Optical Coherence Tomography Images," IEEE Transactions on Medical Imaging, vol. 28, No. 9, Sep. 2009, pp. 1436-1447.

Garvin, et al., "Intraretinal Layer Segmentation of Macular Optical Coherence Tomography Images Using Optimal 3-D Graph Search," IEEE Transactions on Medical Imaging, vol. 27, No. 10, Oct. 2008, pp. 1495-1505 (26 pgs.).

Guo, et al., "Automated segmentation of retinal layer boundaries and capillary plexuses in wide-field optical coherence tomographic angiography," Biomedical Optics Express, vol. 9, No. 9, Sep. 2018, pp. 4429-4442.

Guo, et al., "Development and validation of a deep learning algorithm for distinguishing the nonperfusion area from signal reduction artifacts on OCT angiography," Biomedical Optics Express, vol. 10, No. 7, Jul. 2019, pp. 3257-3268.

Guo, et al., "MEDnet, a neural network for automated detection of avascular area in OCT angiography," Biomedical Optics Express, vol. 9, No. 11, Nov. 2018, pp. 5147-5158.

Huang, et al., "Optical Coherence Tomography," Science, vol. 254, No. 5035, Nov. 1991, pp. 1178-1181 (12 pgs.).

Hwang, et al., "Automated Quantification of Nonperfusion Areas in 3 Vascular Plexuses With Optical Coherence Tomography Angiography in Eyes of Patients With Diabetes," JAMA Ophthalmology, vol. 136, No. 8, Jun. 2018, pp. 929-936.

Hwang, et al., "Visualization of 3 Distinct Retinal Plexuses by Projection-Resolved Optical Coherence Tomography Angiography in Diabetic Retinopathy," JAMA Ophthalmology, vol. 134, No. 12, Dec. 2016, pp. 1411-1419 (17 pgs.).

Ip, et al., "Long-term Effects of Therapy with Ranibizumab on Diabetic Retinopathy Severity and Baseline Risk Factors for Worsening Retinopathy," Ophthalmology, vol. 122, No. 2, Feb. 2015, pp. 367-374.

Ishikawa, et al., "Macular Segmentation with Optical Coherence Tomography," Investigative Ophthalmology and Visual Science, vol. 46, No. 6, Jun. 2005, pp. 2012-2017.

Jia, et al., "Split-spectrum amplitude-decorrelation angiography with optical coherence tomography," Optics Express, vol. 20, No. 4, Feb. 2012, pp. 4710-4725.

Jia, et al., "Quantitative optical coherence tomography angiography of choroidal neovascularization in age-related macular degeneration," Ophthalmology, vol. 121, No. 7, Jul. 2014, pp. 1435-1444 (22 pgs.).

Jia, et al., "Quantitative optical coherence tomography angiography of vascular abnormalities in the living human eye," PNAS USA, vol. 112, No. 18, Apr. 2015, pp. E2395-E2402.

Joshi, et al., "Optic Disk and Cup Segmentation from Monocular Color Retinal Images for Glaucoma Assessment," IEEE Transactions on Medical Imaging, vol. 30, No. 6, Jun. 2011, pp. 1192-1205.

Kajic, et al., "Robust segmentation of intraretinal layers in the normal human fovea using a novel statistical model based on texture and shape analysis," Optics Express, vol. 18, No. 14, Jul. 2010, pp. 14730-14744.

Koozekanani, et al., "Retinal Thickness Measurements from Optical Coherence Tomography Using a Markov Boundary Model," IEEE Transactions on Medical Imaging, vol. 20, No. 9, Sep. 2001, pp. 900-916.

Lang, et al., "Retinal layer segmentation of macular OCT images using boundary classification," Biomedical Optics Express, vol. 4, No. 7, Jul. 2013, pp. 1133-1152.

Li, et al., "Optimal Surface Segmentation in Volumetric Images—A Graph-Theoretic Approach," IEEE Transactions on Pattern Analysis and Machine Intelligence, vol. 28, No. 1, Jan. 2006, pp. 119-134 (39 pgs).

Liu, et al., "Automated choroidal neovascularization detection algorithm for optical coherence tomography angiography," Biomedical Optics Express, vol. 6, No. 9, Sep. 2015, pp. 3564-3575.

Mishra, et al., "Intra-retinal layer segmentation in optical coherence tomography images," Optics Express, vol. 17, No. 26, Dec. 2009, pp. 23719-23728.

Raiji, et al., "Future Directions in Retinal Optical Coherence Tomography," retrieved on Jul. 13, 2021, at <<https://www.retinalphysician.com/issues/2012/May 2012/future-directions-in-retinal-optical-coherence-tom>>, Retinal Physician, vol. 9, May 2012, pp. 33-37 (7 pgs. ).

Rathke, et al., "Probabilistic Intra-Retinal Layer Segmentation in 3-D OCT Images Using Global Shape Regularization," Medical Image Analysis, vol. 18, No. 5, Mar. 2014, pp. 781-794 (35 pgs.).

Roy, et al., "ReLayNet: retinal layer and fluid segmentation of macular optical coherence tomography using fully convolutional networks," Biomedical Optics Express, vol. 8, No. 8, Aug. 2017, pp. 3627-3642.

Shi, et al., "Automated 3-D Retinal Layer Segmentation of Macular Optical Coherence Tomography Images with Serous Pigment Epithelial Detachments," IEEE Transactions on Medical Imaging, vol. 34, No. 2, Feb. 2015, pp. 441-452.

Srinivasan, et al., "Automatic segmentation of up to ten layer boundaries in SD-OCT images of the mouse retina with and without missing layers due to pathology," Biomedical Optics Express, vol. 5, No. 2, Feb. 2014, pp. 348-365.

Vermeer, et al., "Automated segmentation by pixel classification of retinal layers in ophthalmic OCT images," Biomedical Optics Express, vol. 2, No. 6, Jun. 2011, pp. 1743-1756.

Yazdanpanah, et al., "Segmentation of Intra-Retinal Layers from Optical Coherence Tomography Images using an Active Contour Approach," IEEE Transactions on Medical Imaging, vol. 30, No. 2, Feb. 2011, pp. 484-496.

Zhang, et al., "Advanced image processing for optical coherence tomographic angiography of macular diseases," Biomedical Optics Express, vol. 6, No. 12, Dec. 2015, pp. 4661-4675.

IDENTIFYING RETINAL LAYER BOUNDARIES

CROSS-REFERENCE TO RELATED APPLICATION

This application claims the benefit of U.S. Application No. 62/889,917, filed on Aug. 21, 2019, which is incorporated by reference herein in its entirety.

STATEMENT REGARDING FEDERALLY SPONSORED RESEARCH

This invention was made with government support under R01 EY027833 awarded by the National Institutes of Health. The government has certain rights in the invention.

TECHNICAL FIELD

This disclosure relates generally to systems, devices, and methods for identifying retinal layer boundaries in optical coherence tomography (OCT) images.

BACKGROUND

Optical coherence tomography (OCT) (D. Huang, et al., SCIENCE 254(5035), 1178-1181 (1991)) is an interferometric imaging technology capable of acquiring high resolution, three-dimensional (3D) images of biological tissue such as the retina through non-invasive and non-contact laser scanning. It has been widely used in the diagnosis of ophthalmic diseases, such as glaucoma (D. Huang, et al., SCIENCE 254 (5035), 1178-1181 (1991)), diabetic retinopathy (DR) (J. C. Bavinger, et al., INVESTIGATIVE OPHTHALMOLOGY AND VISUAL SCIENCE 57(1), 208-217 (2016)), and age-related macular degeneration (AMD) (H. R. Coleman, et al., LANCET 372(9652), 1835-1845 (2008)), by quantifying the thicknesses of relevant slabs. OCT angiography (OCTA) is a new clinical tool for the early diagnosis of the diseases affecting retinal circulation and assessment of progression. Based on the variation of OCT signals between B-scans (e.g., two-dimensional (2D) depth images of a retina extending parallel to a depth direction) at the same relative position, OCTA can provide depth-resolved flow signals for microvasculature in the retina. Prior studies have suggested that slab-based OCTA can improve the visualization and interpretation of OCTA volumes (J. P. Campbell, et al., SCIENTIFIC REPORTS 7 (January), 42201 (2017); Y. Jia, et al., PROCEEDINGS OF THE NATIONAL ACADEMY OF SCIENCES 112(18), E2395-E2402 (2015); Y. Jia, et al., OPHTHALMOLOGY 121(7), 1435-1444 (2014)). A recent study also showed that vascular abnormalities are better visualized using OCTA by separating the retinal circulation into three vascular layers (T. S. Hwang, et al., JAMA OPHTHALMOLOGY 134(12), 1411-1419 (2016); T. S. Hwang, et al., JAMA OPHTHALMOLOGY 97239(8), 929-936 (2018)). Therefore, automated segmentation of the retinal layer boundaries can be used to accurately assess anatomic thickness and capillary plexuses.

The segmentation of retinal layers is a challenging task that has been approached through a diversity of methods. Various approaches exploit the reflectance contrast between adjacent retinal layers to distinguish them (D. C. DeBuc, IMAGE SEGMENTATION, P.-G. Ho, ed. (InTech, 2011), pp. 15-54; D. Koozekanani, et al., IEEE TRANSACTIONS ON MEDICAL IMAGING 20(9), 900-916 (2001); D. C. Fernández, et al., OPTICS EXPRESS 13(25), 10200-10216 (2005)). Some methods have relied on the gradient information for active contour (A. Mishra, et al., OPTICS EXPRESS 17(26), 23719-28 (2009); A. Yazdanpanah, et al., IEEE TRANSACTIONS ON MEDICAL IMAGING 30(2), 484-96 (2011)). Some methods utilize graph search techniques (S. J. Chiu, et al., OPTICS EXPRESS 18(18), 19413 (2010); P. P. Srinivasan, et al., BIOMEDICAL OPTICS EXPRESS 5(2), 348 (2014); M. Zhang, et al., BIOMEDICAL OPTICS EXPRESS 6(12), 4661 (2015); M. K. Garvin, et al., IEEE TRANSACTIONS ON MEDICAL IMAGING 27(10), 1495-1505 (2008)). Some approaches have relied on training supervised machine learning methods such as the support vector machine (K. a Vermeer, et al., BIOMEDICAL OPTICS EXPRESS 2(6), 1743-1756 (2011)), random forests (A. Lang, et al., BIOMEDICAL OPTICS EXPRESS 4(7), 1133 (2013)), deep learning (L. Fang, et al., BIOMEDICAL OPTICS EXPRESS 8(5), 2732-2744 (2017); A. G. Roy, et al., BIOMEDICAL OPTICS EXPRESS 8(8), 3627-3642 (2017)), probability-based approach (F. Rathke, et al., MEDICAL IMAGE ANALYSIS 18(5), 781-794 (2014)), and other methods (H. Ishikawa, et al., INVESTIGATIVE OPHTHALMOLOGY AND VISUAL SCIENCE 46(6), 2012-2017 (2005); V. Kajić, et al., OPTICS EXPRESS 18(14), 14730-14744 (2010); M. Baroni, et al., MEDICAL ENGINEERING AND PHYSICS 29(4), 432-441 (2007); B. Antony, et al., BIOMEDICAL OPTICS EXPRESS 2(8), 2403-2416 (2011); Q. Dai, et al., 2011 4TH INTERNATIONAL CONFERENCE ON BIOMEDICAL ENGINEERING AND INFORMATICS (BMEI) (IEEE, 2011), 57(10), pp. 142-146; F. Shi, et al., IEEE TRANSACTIONS ON MEDICAL IMAGING 34(2), 441-452 (2015)).

With increasing advancements in swept-source OCT (SS-OCT) technology, wide-field OCT imaging has been enabled to evaluate larger portions of the retina (V. Raiji, et al., RETINAL PHYSICIAN 9, 33-37 (2012)). However, the wide-field OCT poses new challenges to the existing segmentation algorithms. First, SS-OCT systems, using 1050-nm center wavelength lasers, have decreased the axial resolution and back-scattered reflectance contrast compared to those of the spectral domain commercial devices that use 840-nm center wavelength. This reduces the pixels contained within retinal layers as well as the number of features that can be extracted for machine learning segmentation alternatives. Second, due to the large retinal curvature-associated aberration in the wider field of view, the focusing of wide-field OCT is compromised in the peripheral regions. Third, retinal curvature and anatomic variations are increased as the field of view increases. These characteristics make single source path search algorithms (e.g., graph search) prone to local errors that can be propagated further by the search routine.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The detailed description is described with reference to the accompanying figures. In the figures, the left-most digit(s) of a reference number identifies the figure in which the reference number first appears. The use of the same reference numbers in different figures indicates similar or identical components or features.

FIGS. 11A to 11O illustrates an example of search guidance points in an A-scan.

DETAILED DESCRIPTION

Figure 1:
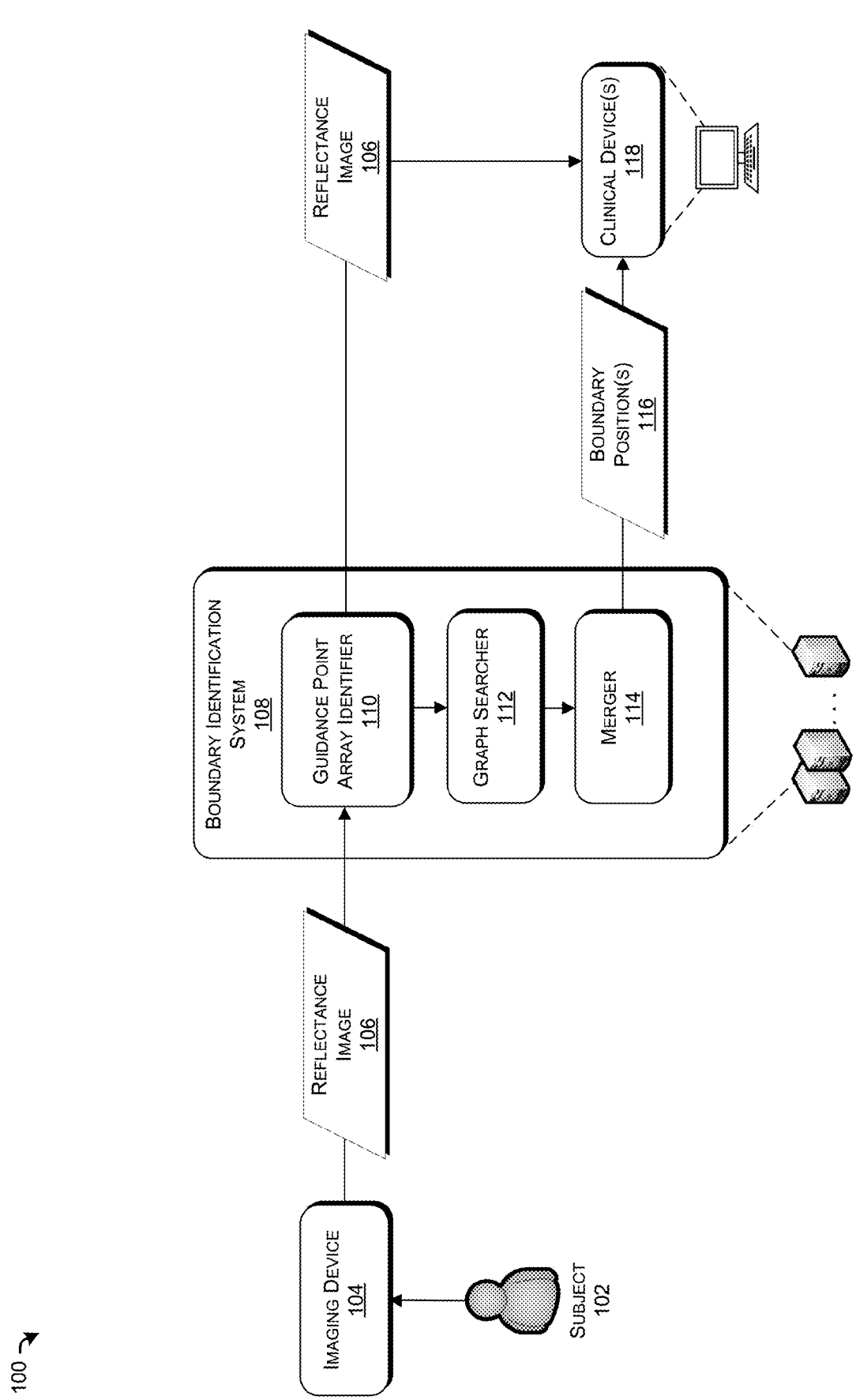
FIG. 1 illustrates an example environment for performing automated segmentation of retinal layers in a subject.

This disclosure describes systems, devices, and techniques for automatically identifying the position(s) of retinal layer boundaries of a subject based on a reflectance image of the subject's retina. In various implementations disclosed herein, the positions of the retinal layer boundaries are accurately identified from a wide-field OCT or OCTA scan (e.g., a scan with a larger field of view than a 3×3 mm or 6×6 mm scan). Identifying positions of retinal layer boundaries is also referred to as "segmentation," in some cases described herein.

Prior studies have demonstrated a successful segmentation technique based on directional graph search for 3×3- and 6×6-mm scans of the retina (M. Zhang, et al., BIOMEDICAL OPTICS EXPRESS 6(12), 4661 (2015)). To address the challenges associated with wide-field scans, various implementations disclosed herein use a Guided Bidirectional Graph Search (GB-GS) method, in which an array of points is used to guide the graph search technique in multiple directions to identify various retinal boundaries.

Some example implementations of the segmentation technique utilize three steps. In an example first step, a guidance point array (GPA) is identified to represent the approximate positions of a particular boundary. Then, in an example second step, a bidirectional graph search is applied to various points contained in the GPA to generate one or more candidate paths representing the boundary. In an example third step, the candidate paths that are closest to the GPA can be used to identify the position of the boundary.

Various implementations identify GPAs corresponding to different retinal layer boundaries using gradient maps. In some cases, gradient maps are generated based on differentials between reflectance values of pixels of a reflectance image that are adjacent. In some cases, the pixels are adjacent (e.g., bordering one another) in a direction corresponding to a direction that is parallel to the scanning beam of the OCT incident on the retina. For instance, the pixels may be adjacent in a direction that is parallel to a depth direction (e.g., a direction extending between a vitreous layer and a Bruch's membrane of the retina). In some cases, a gradient map is generated based on light-to-dark transitions or dark-to-light transitions between pairs of pixels in the reflectance image.

According to some instances, GPAs corresponding to different retinal layer boundaries are identified based on different types of gradient maps (e.g., light-to-dark or dark-to-light gradient maps), due to the physics of reflectance imaging and the natural physiology of the retina. For example, the light-to-dark gradient map is used to identify GPAs corresponding to a vitreous/ILM boundary, an INL/OPL boundary, and an upper EZ boundary in the retina. In some instances, the dark-to-light gradient map is used to identify GPAs corresponding to an NFL/GCL boundary, an IPL/IN boundary, an OPL/ONL boundary, and an RPE/BM boundary.

In some examples, the GPAs are identified in a predefined order. For instance, a GPA corresponding to a vitreous/ILM boundary is identified first, then a GPA corresponding to an upper EZ boundary is identified second, a GPA corresponding to an RPE/BM boundary is identified third, a GPA corresponding to an OPL/ONL boundary is identified fourth, a GPA corresponding to an IPL/INL boundary is identified fifth, a GPA corresponding to an NFL/GCL boundary is identified sixth, and a GPA corresponding to an INL/OPL boundary is identified seventh. In various implementations, an individual GPA is identified based on the gradient maps and positions of one or more other GPAs that have been previously identified. Various computer-implemented implementations of this sequential GPA identification process are used to increase the accuracy of the final identified boundaries using a limited amount of processing resources.

In various examples, a bidirectional graph search of the reflectance image is used to identify multiple candidate paths corresponding to the boundary. In some examples, for any initial search point in an initial A-line of the reflectance image, multiple candidate points are identified in a new A-line adjacent to the initial A-line. A particular point in the multiple candidate points corresponding to a minimum gradient between the reflectance value of the initial search point and the reflectance values of the candidate points is selected as the next search point, in some instances. According to some examples, both search points are defined in a candidate path corresponding to the boundary. In some cases, the candidate points are identified in two A-lines adjacent to the initial A-line in two directions (e.g., the A-line to the right of the initial A-line and to the left of the initial A-line), such that the search progresses in two directions from the initial search point.

In particular implementations, the bidirectional graph search used to identify multiple candidate paths of a boundary is initialized in multiple places in the reflectance image, such as multiple positions throughout the GPA corresponding to the boundary. In some cases, if a first candidate path diverges from the GPA, the bidirectional graph search is reinitialized at a position of the GPA that is not represented in the first candidate path, thereby generating a second candidate path. The multiple candidate paths are merged based on the GPA, in some cases. For instance, the position of the boundary is approximated by segments of the candidate paths that are nearest to the originally defined GPA.

Various implementations described herein are directed to specific improvements in the technical field of retinal imaging. For instance, as provided below in an Example, various implementations more accurately identify boundaries between retinal layers than other, previously disclosed automated methods. That is, various implementations can be used to more closely approximate the boundaries that are defined, manually, by experts.

Unlike manual segmentation, however, various implementations described herein can be performed automatically using computer-based methods. Thus, particular implementations described herein can be used to perform accurate retinal layer segmentation on subjects that do not have access to the highly specialized care providers trained to perform manual segmentation.

In addition, various implementations described herein are performed more efficiently than machine-learning-based methods. For instance, automated segmentation performed according to implementations described herein utilize a smaller amount of memory and processing resources than other segmentation methods that require machine learning. Further, some implementations described herein do not require large training data sets to accurately identify the positions of retinal layer boundaries in a subject, unlike machine-learning-based methods.

In various examples of the present disclosure, the positions of boundaries between different layers of the retina are accurately identified from wide-field OCT scans. Unlike previous methods, implementations described herein accurately segment retinas even with the decreased axial resolution and back-scattered reflectance contrast, reduced focus, increased retinal curvature and anatomic variation of wide-field OCT.

Example Definitions

As used herein, the term "segmentation," and its equivalents, can refer to a process of defining an image of a retina into regions corresponding to different retinal layers. For instance, a segmentation method can be performed by defining the positions of boundaries between layers of the retina.

As used herein, the term "reflectance image" can refer to a two-dimensional B-scan of a retina, wherein the values of individual pixels of the reflectance image correspond to reflectance intensity values observed by an OCT system at respective positions corresponding to the individual pixels. One dimension of the B-scan can be defined along a depth direction. Another direction can be defined along a lateral direction of the retina (e.g., defined in a direction parallel to a direction defined between the eyes of the subject).

As used herein, the term "depth direction," and its equivalents, can refer to a direction in a reflectance image that is parallel to a direction extending between a vitreous and a Bruch's membrane of a retina depicted in the reflectance image. The depth direction may be parallel to an OCT beam incident on the retina, in some cases.

As used herein, the terms "A-line," "A-scan," and their equivalents, can refer to a one-dimensional set of pixels in a reflectance image. In particular, an A-line can extend in a direction parallel to a depth direction. A reflectance image can comprise multiple A-lines. A length of an A-line may be the same length as the reflectance image, and a width of the A-line may be a width of a single pixel length.

As used herein, the term "OCT image," and its equivalents, can refer to an OCT reflectance image, an OCTA image, or a combination thereof.

As used herein, the terms "wide-field OCT image," "wide-field OCT scan," and their equivalents, can refer to an OCT image with a field of view that is greater than 3×3 mm, 4×4 mm, 5×5 mm, or 6×6 mm.

As used herein, the term "GPA" can refer to a set of positions of pixels in a reflectance image that approximate the position of a particular retinal layer boundary. A GPA can be used to guide a graph search for the identification of the position of the retinal layer boundary.

As used herein, the term "graph search" can refer to a process by which an additional point in a retinal boundary can be approximated based on a reference point, wherein the additional point and the reference point are adjacent to each other and both present in a reflectance image of the retina. The additional point and the reference point are both pixels in the reflectance image, in some cases. A "bidirectional graph search" can refer to a process by which a graph search is performed in two directions from a given reference point. A "guided graph search" can refer to a graph search process by which the position of a boundary is estimated based on guidance from a predefined GPA approximating the position of the boundary.

As used herein, the terms "candidate path," "candidate graph," and their equivalents can refer to a set of positions of pixels in a reflectance image that are generated using a graph search and that approximate a potential position of a retinal layer boundary in the reflectance image.

As used herein, the term "kernel," and its equivalents, can refer to a function, such as applying a filter, performed by a neuron on a portion of an input to a block.

As used herein, the term "pixel," and its equivalents, can refer to a value that corresponds to an area or volume of an image. In a grayscale image, the value can correspond to a grayscale value of an area of the grayscale image. In a color image, the value can correspond to a color value of an area of the color image. In a binary image, the value can correspond to one of two levels (e.g., a 1 or a 0). The area or volume of the pixel may be significantly smaller than the area or volume of the image containing the pixel. In examples of a line defined in an image, a point on the line can be represented by one or more pixels.

Particular Implementations

Some particular implementations of the present disclosure will now be described with reference to FIGS. 1 to 7. However, the implementations described with reference to FIGS. 1 to 7 are not exhaustive.

FIG. 1 illustrates an example environment 100 for performing automated segmentation of retinal layers in a subject 102. In some examples, the subject 102 is a human or non-human animal. In particular instances, the subject 102 is a patient at a healthcare facility, such as a clinic, hospital, or the like.

With reference to the example environment 100, an imaging device 104 is configured to obtain a reflectance image 106 of a retina of the subject 102. The imaging device 104 is an OCT imaging system, in various examples. In some cases, the imaging device 104 also includes functionality to obtain an OCTA image of the retina of the subject 102.

According to some examples, the reflectance image 106 is a B-scan of the retina of the subject 102. In some implementations, the reflectance image 106 obtained by the imaging device 104 is a wide-field OCT image. For example, the reflectance image 106 can be have a field of view that is wider than 6 mm in one direction.

In various implementations, the imaging device 104 provides the reflectance image 106 to a boundary identification system 108. In some cases, the imaging device 104 is integrated into the boundary identification system 108. In some examples, the imaging device 104 transmits the reflectance image 106 to the boundary identification system 108 over one or more communication networks in the form of one or more data packets.

The boundary identification system 108 is configured to identify retinal layer boundaries in the retina of the subject 102 based on the reflectance image 106. In various examples. The boundary identification system 108 includes a guidance point array identifier 110, a graph searcher 112, and a merger 114.

In various examples, the guidance point array identifier 110 is configured to generate one or more guidance point arrays respectively corresponding to one or more retinal layer boundaries depicted in the reflectance image 106. For instance, the guidance point array identifier 110 generates a first guidance point array corresponding to a first retinal layer boundary, a second guidance point array corresponding to a second retinal layer boundary, and so on. In some examples, the one or more retinal layer boundaries include at least one of a vitreous/inner limiting membrane (ILM) boundary, an inner nuclear layer (INL)/outer plexiform layer (OPL) boundary, an upper ellipsoid zone (EZ) boundary, a nerve fiber layer (NFL)/ganglion cell layer (GCL) boundary, an inner plexiform layer (IPL)/inner nuclear layer (INL) boundary, an OPL/outer nuclear layer (ONL) boundary, or a retinal pigment epithelium (RPE)/Bruch's membrane (BM) boundary.

In particular implementations, the guidance point array identifier 110 generates one or more gradient maps corresponding to the reflectance image 106. For instance, the guidance point array identifier 110 generates a light-to-dark gradient map by identifying an amount of a light-to-dark transition between each adjacent (e.g., in a depth direction) pair of pixels in the reflectance image 106 and generates a dark-to-light gradient map by identifying an amount of a dark-to-light transition between each adjacent pair of pixels in the reflectance image 106. Each gradient map has the same pixel dimensions as the reflectance image 106, in various implementations.

In some cases, the guidance point array identifier 110 identifies multiple guidance point arrays, corresponding to different retinal layer boundaries, based on the gradient map(s). For instance, the guidance point array identifier 110 identifies at least one guidance point array corresponding to at least one of vitreous/ILM, INL/OPL, or upper EZ boundaries using the light-to-dark gradient map. In some examples, the guidance point array identifier 110 identifies at least one guidance point array corresponding to at least one of NFL/GCL, IPL/INL, OPL/ONL, or RPE/BM boundaries using the dark-to-light gradient map. An individual guidance point array is obtained, for example, based on maximum reflectance values in one of the gradient maps. In some cases, points in an individual guidance point array are identified in multiple A-lines throughout the reflectance image 106 (and/or gradient map(s), which may have the same dimensions as the reflectance image 106). For example, the guidance point array includes points in every A-line, every other A-line, every third A-line, every fourth A-line, every fifth A-line, or the like.

According to various implementations, the guidance point array identifier 110 identifies guidance point arrays in a predetermined order. As a result, in some examples, a particular guidance point array of a particular boundary are identified based, at least in part, on one or more guidance point arrays that have been previously identified. In some cases, the guidance point arrays for various retinal layer boundaries are obtained by the guidance point array identifier 110 in the following search order: vitreous/ILM, upper EZ, RPE/BM, OPL/ONL, IPL/INL, INF/GCL, and finally, INL/OPL. For example, the guidance point array for the upper EZ boundary can be obtained based at least in part on the guidance point array corresponding to the vitreous/ILM boundary, the guidance point array for the RPE/BM boundary can be obtained based at least in part on at least one guidance point array corresponding to at least one of the vitreous/ILM boundary or the upper EZ boundary, and so on. Accordingly, the identification of guidance point arrays corresponding to boundaries that appear with a relatively low contrast in the reflectance image 106 and/or the gradient map(s) can be enhanced based on estimations of other boundaries in the retina and on a predetermined order of retinal layers (e.g., based on known retinal physiology).

In some cases, the guidance point array identifier 110 identifies one or more of the guidance point arrays (e.g., corresponding to the vitreous/ILM and upper EZ boundaries) using an enhanced version of the reflectance image 106. The guidance point array identifier 110 enhances the reflectance image 106 is, in particular examples, by normalizing the reflectance image 106, adding a gradient map (e.g., the light-to-dark gradient map) to the normalized version of the reflectance image 106, and binarizing the summed image based on a threshold that is defined as the average reflectance value of the summed image. For instance, the pixels in the summed image with values that are below the average reflectance value are redefined to have values of zero, and the pixels in the summed image with values that are above or equal to the average reflectance value are redefined to have values of one.

The guidance point array identifier 110, in some examples, applies a horizontal gradient operator to one or more of the obtained guidance point arrays. In some cases, the guidance point array identifier 110 filters each guidance point array. For instance, the guidance point array identifier 110 removes unreliable points from the guidance point array by applying a mean filter on the guidance point array.

In some implementations, the graph searcher 112 is configured to generate candidate paths corresponding to each boundary using a graph search technique. In an example of a graph search technique, the graph searcher 112 identifies a first point (e.g., a pixel) of the reflectance image 106 on a candidate path, identifies multiple (e.g., 2-7) candidate points adjacent to the first point, identifies differences between the reflectance value of the first point and the reflectance values of the candidate points, identifies a second point among the candidate points associated with the minimum difference, and defines the second point as part of the candidate path. According to various implementations, the graph searcher 112 performs the graph search technique recursively, such that the second point becomes the first point and is used to identify another point in the candidate path.

According to some examples, the graph searcher 112 generates the multiple candidate paths by initiating the graph search technique at multiple initial starting points. In some cases, the starting points can include a virtual point outside of the image. In some examples, the starting points can include one or more points on the corresponding guidance point array. According to certain implementations, the graph searcher 112 performs the graph search technique from starting points where previously obtained candidate paths diverge from the corresponding guidance point array. For instance, a first candidate path may diverge (e.g., by a threshold of one to twenty pixels) from the guidance point array at a first point on the first candidate path, and the graph searcher 112 may obtain a second candidate path by initiating a graph search technique at a starting point at the first point or at a second point in a portion of the guidance point array that diverges from the first candidate path.

In various implementations, the graph searcher 112 performs a guided bidirectional graph search technique to obtain the candidate paths for each boundary. In an example of the guided bidirectional graph search technique, the graph searcher 112 identifies additional pixels in a candidate path based on candidate pixels in A-lines of the reflectance image 106 adjacent to the starting pixel in two directions (e.g., left and right) from an initial pixel.

The merger 114 is configured to identify the position of each boundary by merging the multiple candidate paths corresponding to the boundary, in various implementations. In some examples, the merger 114 defines one or more segments of the guidance point array and/or the candidate paths that overlap in a depth direction (e.g., a vertical direction if the vitreous is depicted toward the top of the reflectance image 106 and the Bruch's membrane is depicted toward the bottom of the reflectance image 106). Each one of these segments is defined between two points on or within a predetermined number of pixels (e.g., 2-5 pixels) of the guidance point array. The merger 114 identifies the position of the boundary between those two points by comparing the segment of the guidance point array to the segments of the candidate paths that overlap the segment of the guidance point array. The candidate path whose segment is the closest to the guidance point array is used, by the merger 114, to define a portion of the position of the boundary. The merger 114 identifies the segments of the position of the boundary consecutively throughout the reflectance image, in particular implementations. In some cases, at least one identified retinal layer boundary can be further utilized to identify position(s) of capillary plexuses depicted in the reflectance image 106.

In various examples, the boundary identification system 108 transmits an indication of at least one boundary position 116, corresponding to at least one retinal layer boundary, to one or more clinical devices 118. In some cases, the boundary identification system 108 and/or the imaging device 104 transmit the reflectance image 106 to the clinical device(s) 118. The clinical device(s) 118, upon receiving the boundary position(s) 116, may output the boundary position(s) 116. In some cases, the clinical device(s) 118 display the boundary position(s) 116 overlaid on the reflectance image 106. Using the boundary position(s) 116 and/or the reflectance image 106, a care provider (e.g., a physician) can diagnose a problem with the retina of the subject 102 or confirm that the retina of the subject 102 is healthy. In various implementations, the clinical device(s) 118 include at least one of a mobile device, a user device, a computer, a tablet, a mobile phone, a personal digital assistant, or the like.

In some cases, the clinical device(s) 118 utilize the boundary position(s) 116 to generate an OCTA image of the retina. For instance, the boundary position(s) 116 can be used to enhance a machine-learning based approach for identifying avascular areas of an OCTA image, such as the approaches described in Guo, et al., BIOMED. OPT. EXPRESS 9(11), 5147-58 (2018) and Guo, et al., BIOMED. OPT. EXPRESS 9(11), 3257-68 (2019).

In various implementations, the clinical device(s) 118 identify that the retina of the subject 102 is likely to be diseased and generate one or more recommendations to treat the retina of the subject 102. In some cases, the clinical device(s) 118 identify that the subject 102 has glaucoma, DR, and/or AMD based on the thicknesses of retinal layers defined by the boundary position(s) 116.

Figure 2:
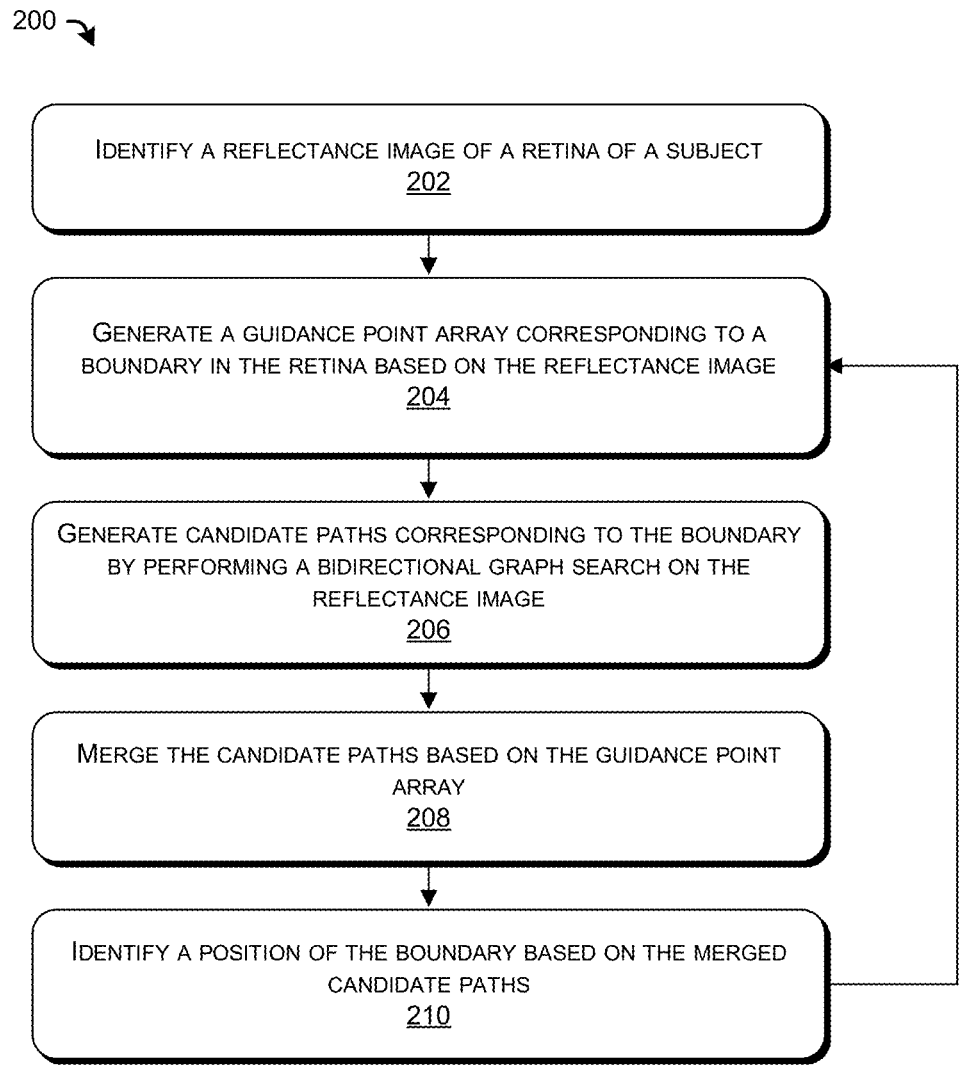
FIG. 2 illustrates a process for identifying the positions of boundaries in retina based on a reflectance image of the retina.

FIG. 2 illustrates a process 200 for identifying the positions of boundaries in retina based on a reflectance image of the retina. In various implementations, process 200 is performed by a system including at least one of an imaging device (e.g., imaging device 104), a boundary identification system (e.g., boundary identification system 108), a guidance point array identifier (e.g., guidance point array identifier 110), or one or more clinical devices (e.g., clinical device(s) 118).

At 202, the system identifies a reflectance image of a retina of a subject. In various implementations, the reflectance image is obtained by the system (e.g., by imaging the retina of the subject) or may be received by another system (e.g., received from an imaging system in a transmission). The reflectance image is a 2D OCT reflectance image representing a depth slice of the retina, in some cases. In various implementations, the reflectance image is a widefield OCT image of the retina.

At 204, the system generates a guidance point array corresponding to a boundary in the retina based on the reflectance image. In some cases, the system generates at least one gradient map of the reflectance image and searches for the guidance point array in the at least one gradient map. In implementations in which the system has previously obtained one or more guidance point arrays corresponding to one or more other boundaries of the retina, a new guidance point array can be obtained based on both the previously obtained guidance point array(s) and the gradient map(s).

At 206, the system generates candidate paths corresponding to the boundary by performing a bidirectional graph search on the reflectance image. In various implementations, the system performs multiple bidirectional graph searches from multiple starting points related to the reflectance image. The starting points can be selected from at least one of a virtual point outside of the reflectance image, a point on the guidance point array, or a point between the guidance point array and a previously obtained candidate path.

At 208, the system merges the candidate paths based on the guidance point array. In some implementations, the system compares first segments of multiple candidate paths that extend between two common points to a second segment of the guidance point array that overlaps the first segments in a depth direction. In some examples, the segment among the first segments that is closest to the second segment is selected. The system performs this process until a single merged path is identified across the width of the reflectance image.

At 210, the system identifies a position of the boundary based on the merged candidate paths. That is, the position of the boundary is defined to overlap each one of the selected segments of the candidate paths.

The system can repeat 204-210 for each one of the boundaries to be identified in the retina. In some cases, the system can perform 204 for each one of the boundaries before moving onto 206-210 for the boundaries.

Figure 3:
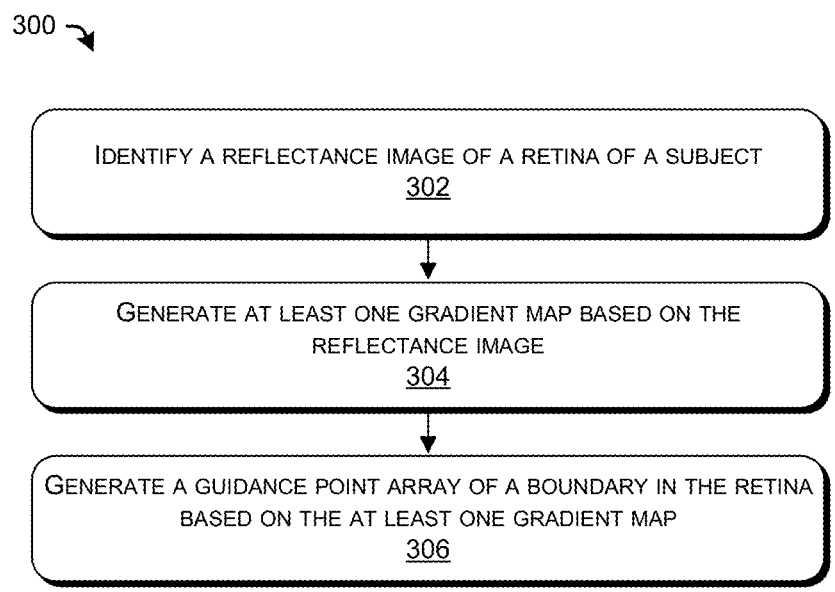
FIG. 3 illustrates a process for determining a guidance point array of a boundary in a retina based on a reflectance image of the retina.

FIG. 3 illustrates a process for determining a guidance point array of a boundary in a retina based on a reflectance image of the retina. In various implementations, process 300 is performed by a system including at least one of an imaging device (e.g., imaging device 104), a boundary identification system (e.g., boundary identification system 108), a guidance point array identifier (e.g., guidance point array identifier 110), or one or more clinical devices (e.g., clinical device(s) 118).

At 302, the system identifies the reflectance image of the retina of a subject. In various implementations, the reflectance image is obtained by the system (e.g., by imaging the retina of the subject) or may be received by another system (e.g., received from an imaging system in a transmission). The reflectance image is a 2D OCT reflectance image representing a depth slice of the retina, in some cases. In various implementations, the reflectance image is a wide-field OCT image of the retina.

At 304, the system generates at least one gradient map based on the reflectance image. In some implementations, the system identifies a light-to-dark gradient map by applying the following Equation 1 to the reflectance image:

$$G(x, z) = I(x, z) - I(x, z-1); x = 1, 2, \ldots, N; z = 1, 2, \ldots, M$$

$$G_A(x, z) = \begin{cases} 1 - G(x, z), & G(x, z) > 0 \\ 1, & \text{otherwise} \end{cases},$$

and
wherein the reflectance image is two-dimensionally defined by an x direction and a z direction, l(x,z) is a reflectance value of the reflectance image of the pixel at position (x,z), M is the length of A-scans in the reflectance image in pixels, N is the width of the reflectance image in pixels, and $G_A(x, z)$ is a value of the light-to-dark gradient map at position (x, z).

In some implementations, the system identifies a dark-to-light gradient map by applying the following Equation 2 to the reflectance image:

$$G(x, z) = I(x, z) - I(x, z-1); x = 1, 2, \ldots, N; z = 1, 2, \ldots, M$$

$$G_B(x, z) = \begin{cases} 1 - |G(x, z)|, & G(x, z) < 0 \\ 1, & \text{otherwise} \end{cases},$$

and
wherein the reflectance image is two-dimensionally defined in an x direction and a z direction, l(x,z) is a reflectance value of the pixel of the reflectance image at position (x,z), M is the length of A-scans in the reflectance image in pixels, N is the width of the reflectance image in pixels, and $G_B(x, z)$ is a value of the dark-to-light gradient map at position (x, z).

At 306, the system generates a guidance point array corresponding to the boundary in the retina based on the at least one gradient map. For instance, the system generates a guidance point array corresponding to one of the vitreous/ILM, INL/OPL, or upper EZ boundaries based on the light-to-dark gradient map. In some examples, the system generates a guidance point array corresponding to one of the NFL/GCL, IPL/INL, OPL/ONL, or RPE/BM boundaries using the dark-to-light gradient map. In some cases, the system repeats process 300 for each one of the boundaries to be identified in the retina.

Figure 4:
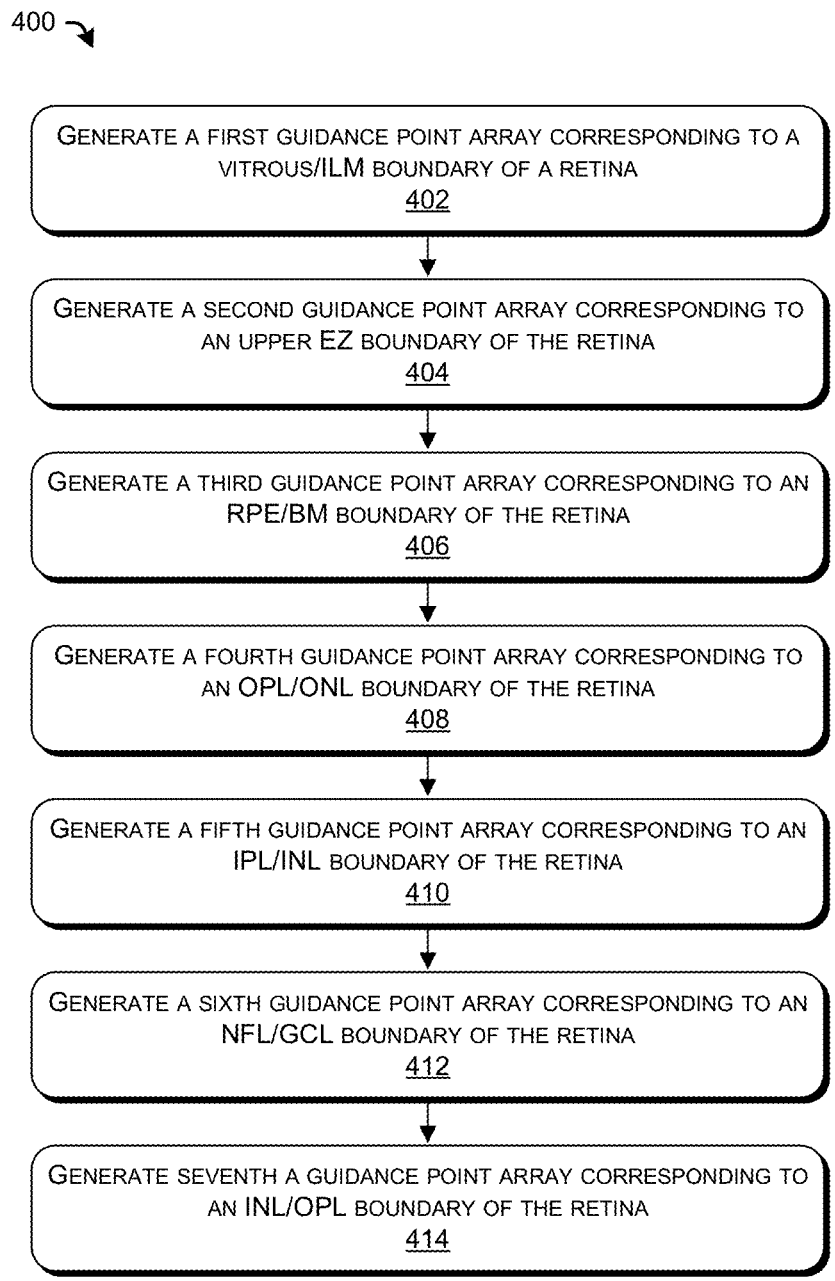
FIG. 4 illustrates a process for determining various guidance point arrays of various boundaries in a retina.

FIG. 4 illustrates a process 400 for determining various guidance point arrays of various boundaries in a retina. In various implementations, process 400 is performed by a system including at least one of an imaging device (e.g., imaging device 104), a boundary identification system (e.g., boundary identification system 108), a guidance point array identifier (e.g., guidance point array identifier 110), or one or more clinical devices (e.g., clinical device(s) 118).

At 402, the system generates a first guidance point array corresponding to a vitreous/ILM boundary of the retina. In various implementations, the system generates the first guidance point array based on a light-to-dark gradient map of a reflectance image of the retina. In some cases, the system adds the light-to-dark gradient map to a normalized version of the reflectance image, binarizes the summed image so that all pixels corresponding to values that are below an average value of the summed image are set to zero, and defines the top layer of nonzero pixels in the binarized image as the first guidance point array.

At 404, the system generates a second guidance point array corresponding to an upper EZ boundary of the retina. In various implementations, the system generates the second guidance point array based on the light-to-dark gradient map. The vitreous ILM boundary or the upper EZ boundary may be defined as the lowest gradient values in each A-line of the light-to-dark gradient map. Accordingly, by determining the two lowest gradient values in each A-line and discarding the gradient values corresponding to the vitreous/ILM boundary, the system can obtain the second guidance point array.

At 406, the system generates a third guidance point array corresponding to an RPE/BM boundary of the retina. In various implementations, the system generates the third guidance point array based on a dark-to-light gradient map of the reflectance image. For instance, the system searches a portion of the dark-to-light gradient map that corresponds to an area below second guidance point array for the third guidance point array. In some examples, the system searches each of multiple A-lines in the portion of the dark-to-light gradient map to identify a pixel corresponding to the minimum gradient value in the portion of the dark-to-light gradient map and defines the third guidance point array to include positions corresponding to each of the identified pixels.

At 408, the system generates a fourth guidance point array corresponding to an OPL/ONL boundary of the retina. In various implementations, the system generates the fourth guidance point array based on dark-to-light gradient map. For instance, the system searches a portion of the dark-to-light gradient map that corresponds to an area between the first guidance point array and the second guidance point array for the fourth guidance point array. In some examples, the system searches each of multiple A-lines in the portion of the dark-to-light gradient map to identify a pixel corresponding to the minimum gradient value in the portion of the dark-to-light gradient map and defines the fourth guidance point array to include positions corresponding to each of the identified pixels.

At 410, the system generates a fifth guidance point array corresponding to an IPL/INL boundary of the retina. In various implementations, the system generates the fifth guidance point array based on the dark-to-light gradient map. For instance, the system searches a portion of the dark-to-light gradient map that corresponds to an area between the first guidance point array and the fourth guidance point array for the fifth guidance point array. In some examples, the system searches each of multiple A-lines in the portion of the dark-to-light gradient map to identify a pixel corresponding to the minimum gradient value in the portion of the dark-to-light gradient map and defines the fifth guidance point array to include positions corresponding to each of the identified pixels.

At 412, the system generates a sixth guidance point array corresponding to an NFL/GCL boundary of the retina. In various implementations, the system generates the sixth guidance point array based on the dark-to-light gradient map. For instance, the system searches a portion of the dark-to-light gradient map that corresponds to an area between the first guidance point array and the fifth guidance point array for the sixth guidance point array. In some examples, the system searches each of multiple A-lines in the portion of the dark-to-light gradient map to identify a pixel corresponding to the minimum gradient value in the portion of the dark-to-light gradient map and defines the sixth guidance point array to include positions corresponding to each of the identified pixels.

At 414, the system generates a seventh guidance point array corresponding to an INL/OPL boundary of the retina. In various implementations, the system generates the seventh guidance point array based on the light-to-dark gradient map. For instance, the system searches a portion of the light-to-dark gradient map that corresponds to an area between the fourth and fifth guidance point arrays for the seventh guidance point array. In some examples, the system searches each of multiple A-lines in the portion of the dark-to-light gradient map to identify a pixel corresponding to the minimum gradient value in the portion of the dark-to-light gradient map and defines the seventh guidance point array to include positions corresponding to each of the identified pixels.

The system may further use the first to seventh guidance point arrays to perform a guided bidirectional search of the reflectance image for the corresponding boundaries.

Figure 5:
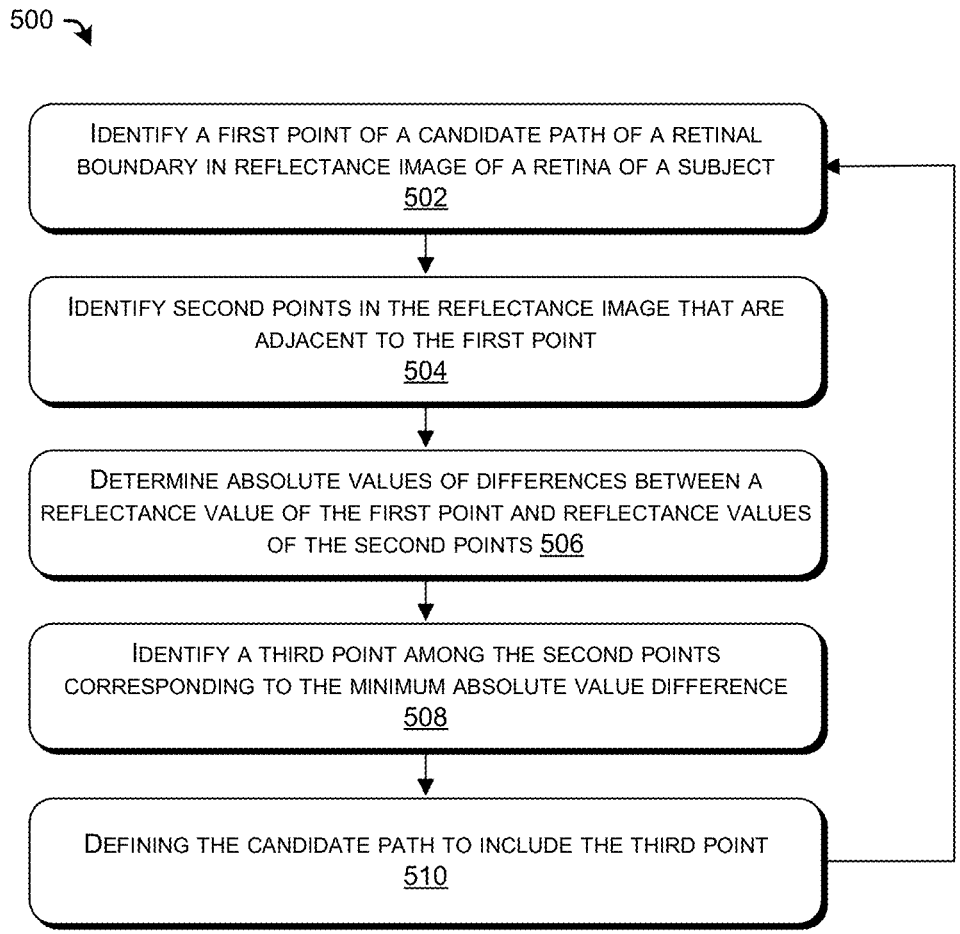
FIG. 5 illustrates a process for identifying multiple candidate paths of a retinal boundary using a graph search technique.

FIG. 5 illustrates a process for identifying multiple candidate paths of a retinal boundary using a graph search technique. In various implementations, process 500 is performed by a system including at least one of an imaging device (e.g., imaging device 104), a boundary identification system (e.g., boundary identification system 108), a graph searcher (e.g., graph searcher 112), or one or more clinical devices (e.g., clinical device(s) 118).

At 502, the system identifies a first point of a candidate path of a retinal boundary in a reflectance image. The reflectance image may represent a retina of a subject. In some cases, the first point is a previously identified point within the candidate path. In some implementations, the first point is a point on a guidance point array corresponding to the retinal boundary.

At 504, the system identifies second points in the reflectance image that are adjacent to the first point. In some cases, the first point is in a first A-line of the reflectance image and the second points are in a second A-line of the reflectance image that is immediately adjacent to the first A-line. In some cases, the second points include the closest 2 to 7 points to the first point in the second A-line.

At 506, the system identifies absolute values of differences between a reflectance value of the first point and reflectance values of the second points. For instance, if the reflectance value of the first point is equal to $r_1$ and the reflectance values of one of the second points is $s_n$, where n is less than or equal to the number of second points, the absolute value of the difference $\Delta_n$ can be obtained using the following Equation 3:

$$\Delta_n = |r_1 - s_n|$$

At 508, the system identifies a third point among the second points corresponding to the minimum absolute value difference. In other words, the third point is one of the second points that has the closest reflectance value to the first point. If the first point is likely to be part of a retinal layer boundary, then the third point is also likely to be part of the same retinal layer boundary.

At 510, the system defines the candidate path to include the third point. In addition, the system may perform the process 500 recursively, such that the third point can be identified as the next first point of the candidate path.

Although process 500 has been described as a unidirectional graph search, in some cases, process 500 can proceed as a bidirectional graph search. For instance, from an initial point of a candidate path (e.g., a point on the guidance point array corresponding to the boundary that is not included in a previously identified candidate path of the boundary), the process 500 can be used to obtain points in the candidate path in two directions from the initial point. In some examples, additional points in the candidate path can be obtained from two different A-lines bordering the A line containing the initial point.

Figure 6:
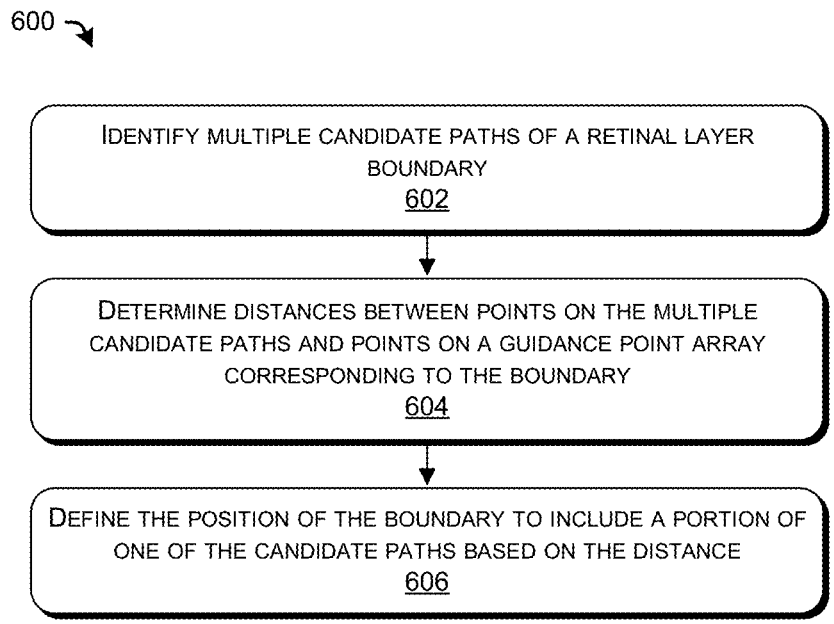
FIG. 6 illustrates a process for determining the position of a retinal layer boundary based on multiple candidate paths.

FIG. 6 illustrates a process 600 for determining the position of a retinal layer boundary based on multiple candidate paths. In various implementations, process 600 is performed by a system including at least one of an imaging device (e.g., imaging device 104), a boundary identification system (e.g., boundary identification system 108), a merger (e.g., merger 114), or one or more clinical devices (e.g., clinical device(s) 118).

At 602, the system identifies multiple candidate paths of a retinal layer boundary. The multiple candidate paths may extend between the same two points. For instance, the candidate paths diverge from each other between the same two points corresponding to positions on a reflectance image of a retina. In some cases, the candidate paths were identified using a (guided bidirectional) graph search process on the reflectance image.

At 604, the system determines distances between points on the multiple candidate paths and points on a guidance point array corresponding to the retinal layer boundary. In particular implementations, the system identifies an A-line between the two points from which the multiple candidate paths diverge. In some cases, the system identifies a distance (e.g., in pixels) between a point in the guidance point array within the A-line and a point in each one of the multiple candidate paths within the A-line. The system may determine average distances between the guidance point array and the multiple candidate paths in a depth direction by identifying multiple A-lines between the two points.

At 606, the system defines the position of the boundary to include a portion of one of the candidate paths based on the distance. For instance, the segment of the candidate path that is closest to the guidance point array between the two points is defined as a segment of the boundary. In some implementations, the system defines the position of the boundary to include multiple segments of multiple divergent candidate paths using the process 600.

Figure 7:
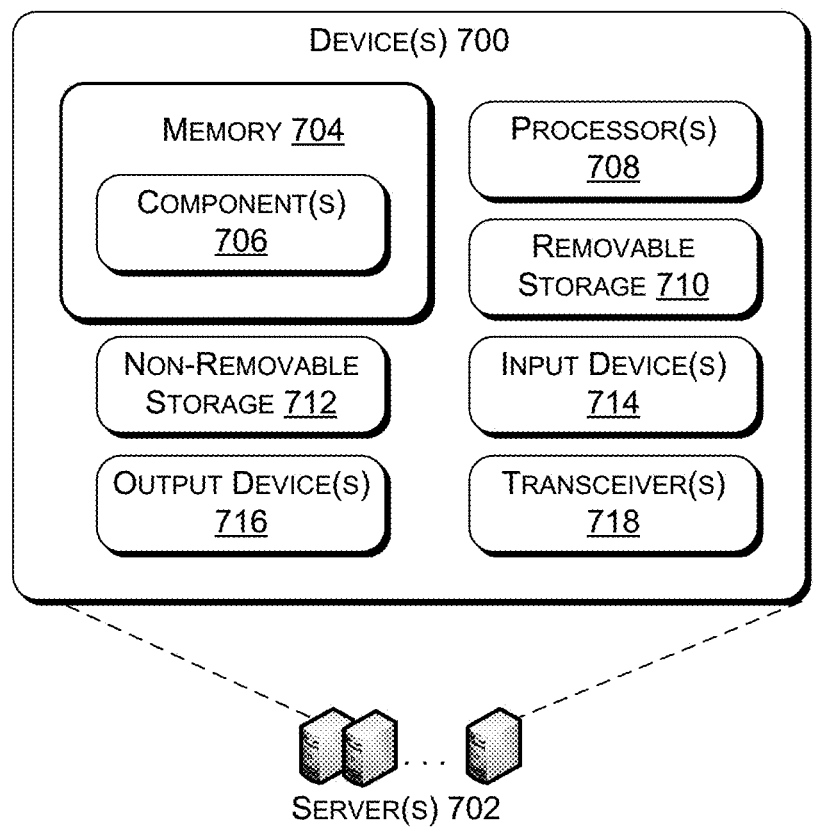
FIG. 7 illustrates an example of one or more devices that can be used to implement any of the functionality described herein.

FIG. 7 illustrates an example of one or more devices 700 that can be used to implement any of the functionality described herein. In some implementations, some or all of the functionality discussed in connection with FIGS. 1-6 can be implemented in the device(s) 700. Further, the device(s) 1100 can be implemented as one or more server computers 702, a network element on a dedicated hardware, as a software instance running on a dedicated hardware, or as a virtualized function instantiated on an appropriate platform, such as a cloud infrastructure, and the like. It is to be understood in the context of this disclosure that the device(s) 700 can be implemented as a single device or as a plurality of devices with components and data distributed among them.

As illustrated, the device(s) 700 include a memory 704. In various embodiments, the memory 704 is volatile (such as RAM), non-volatile (such as ROM, flash memory, etc.) or some combination of the two.

The memory 704 may store, or otherwise include, various components 706. In some cases, the components 706 can include objects, modules, and/or instructions to perform various functions disclosed herein. The components 706 can include methods, threads, processes, applications, or any other sort of executable instructions. The components 706 can include files and databases.

In some implementations, at least some of the components 706 can be executed by processor(s) 708 to perform operations. In some embodiments, the processor(s) 708 includes a Central Processing Unit (CPU), a Graphics Processing Unit (GPU), or both CPU and GPU, or other processing unit or component known in the art.

The device(s) 700 can also include additional data storage devices (removable and/or non-removable) such as, for example, magnetic disks, optical disks, or tape. Such additional storage is illustrated in FIG. 700 by removable storage 710 and non-removable storage 712. Tangible computer-readable media can include volatile and nonvolatile, removable and non-removable media implemented in any method or technology for storage of information, such as computer readable instructions, data structures, program modules, or other data. The memory 704, removable storage 710, and non-removable storage 712 are all examples of computer-readable storage media. Computer-readable storage media include RAM, ROM, EEPROM, flash memory or other memory technology, CD-ROM, Digital Versatile Discs (DVDs), Content-Addressable Memory (CAM), or other optical storage, magnetic cassettes, magnetic tape, magnetic disk storage or other magnetic storage devices, or any other medium which can be used to store the desired information and which can be accessed by the device(s) 700. Any such tangible computer-readable media can be part of the device(s) 700.

The device(s) 700 also can include input device(s) 714, such as a keypad, a cursor control, a touch-sensitive display, a voice input device, etc., and output device(s) 716 such as a display, speakers, printers, etc. In some implementations, the input device(s) 714, in some cases, may include a device configured to capture OCT images, such as OCTA images. In certain examples, the output device(s) 716 can include a display (e.g., a screen, a hologram display, etc.) that can display an OCT image (e.g., an OCTA image) overlaid with an avascular map, thereby indicating portions of the OCT image that correspond to areas of nonperfusion.

As illustrated in FIG. 7, the device(s) 700 can also include one or more wired or wireless transceiver(s) 716. For example, the transceiver(s) 716 can include a Network Interface Card (NIC), a network adapter, a Local Area Network (LAN) adapter, or a physical, virtual, or logical address to connect to the various base stations or networks contemplated herein, for example, or the various user devices and servers. The transceiver(s) 716 can include any sort of wireless transceivers capable of engaging in wireless, Radio Frequency (RF) communication. The transceiver(s) 716 can also include other wireless modems, such as a modem for engaging in Wi-Fi, WiMAX, Bluetooth, or infrared communication.

Example—Automated Segmentation of Retinal Layer Boundaries and Capillary Plexuses in Wide-Field Optical Coherence Tomographic Angiography Advances in retinal layer segmentation of structural optical coherence tomography (OCT) images have allowed the separation of capillary plexuses in OCT angiography (OCTA). With the increased scanning speeds of OCT devices and wider field images (10 mm on fast-axis), greater retinal curvature and anatomic variations have introduced new challenges. This Example illustrates a novel automated method to segment seven retinal layer boundaries and two retinal plexuses in wide-field OCTA images. The automated method was initialized by a series of points forming a guidance point array that estimates the location of retinal layer boundaries. A guided bidirectional graph search method utilizing improvements over previous segmentation techniques was used to search for the precise boundaries. The method was validated on normal and diseased eyes, demonstrating subpixel accuracy for all groups. By allowing independent visualization of the superficial and deep plexuses, this Example illustrates a method that can be used to detect plexus-specific peripheral vascular abnormalities.

1. METHODS 1.1 Data Acquisition

The study was approved by an Institutional Review Board/Ethics Committee of Oregon Health & Science University, and informed consent was collected from all participants, in compliance with the Declaration of Helsinki. Volumetric scans of both eyes of various participants were acquired by a prototype 200-kHz SS-OCT system with a 1050-nm central wavelength covering the 10-mm (fast-axis)×8-mm (slow-axis) retinal regions. Two repeated B-scans were taken at each of 400 raster positions, and each B-scan was comprised of 850 A-lines. B-scans at the same position were averaged to improve signal-to-noise ratio of the structural OCT. The OCTA data was calculated by the split-spectrum amplitude decorrelation angiography (SSADA) technique (as described, e.g., by Y. Jia, et al., OPTICS EXPRESS 20(4), 4710 (2012)).

1.2 Preprocessing

Each B-scan was normalized and then flattened using a center of mass of the B-scan as a reference to prevent errors caused by significant tissue curvature (see, e.g., M. Zhang, et al., BIOMEDICAL OPTICS EXPRESS 6(12), 4661 (2015)). Then, gradient maps were generated to emphasize transitions between retinal layers with different reflectivity. Speckle noise in the gradient maps was reduced by applying a median filter (kernel size 3×3) and a mean filter (kernel size 7×3) that preserved the continuity of layer boundaries.

Figure 8A:
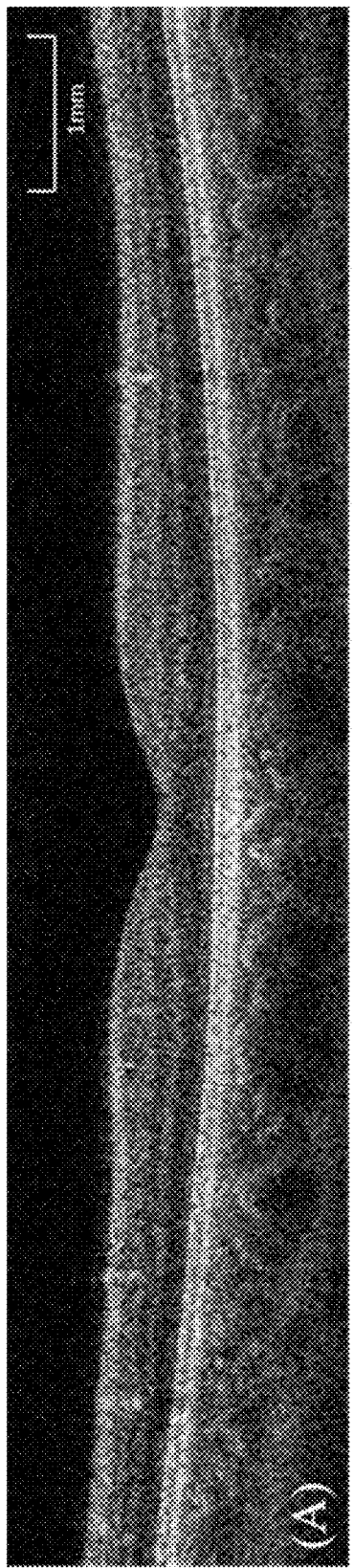
FIGS. 8A and 8B illustrate a representation of retinal layer boundaries that can be segmented by a segmentation method.
Figure 8B:

FIGS. 8A and 8B illustrate a representation of retinal layer boundaries that can be segmented by the automatic segmentation method of this Example. FIG. 8A illustrates a representative wide-field B-scan across the macula of a healthy subject before segmentation. FIG. 8B illustrates segmentation of seven retinal boundaries: ILM (inner limiting membrane), NFL (nerve fiber layer), GCL (ganglion cell layer), IPL (inner plexiform layer), INL (inner nuclear layer) OPL (outer plexiform layer), ONL (outer nuclear layer), EZ (ellipsoid zone), RPE (retinal pigment epithelium), BM (Bruch's membrane). As shown in FIGS. 8A and 8B, the boundaries that were segmented exhibited two different intensity transition modes: light-to-dark and dark-to-light (M. Zhang, et al., BIOMEDICAL OPTICS EXPRESS 6(12), 4661

(2015)). Accordingly, two gradient maps were generated: Gradient Map A ($G_A$) representing dark-to-light transitions and Gradient Map B ($G_B$) representing light-to-dark transitions. The following Equation 4 was used to generate the two gradient maps ($G_A$ and $G_B$):

$$G(x, z) = I(x, z) - I(x, z-1); x = 1, 2, \ldots, N; z = 1, 2, \ldots, M$$

$$G_A(x, z) = \begin{cases} 1 - G(x, z), & G(x, z) > 0 \\ 1, & \text{otherwise} \end{cases}$$

$$G_B(x, z) = \begin{cases} 1 - |G(x, z)|, & G(x, z) < 0 \\ 1, & \text{otherwise} \end{cases}$$

where l(x,z) was the OCT reflectance value at position (x,z), M was the length of A-scans in pixels, and N was the width of B-scans in pixels.

Figure 9A:
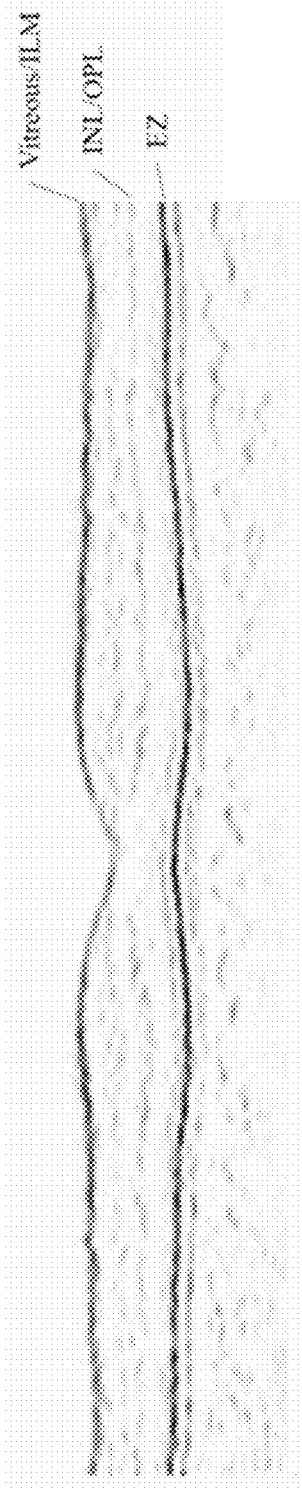
FIGS. 9A and 9B illustrates an example of two gradient maps used for layer segmentation.
Figure 9B:
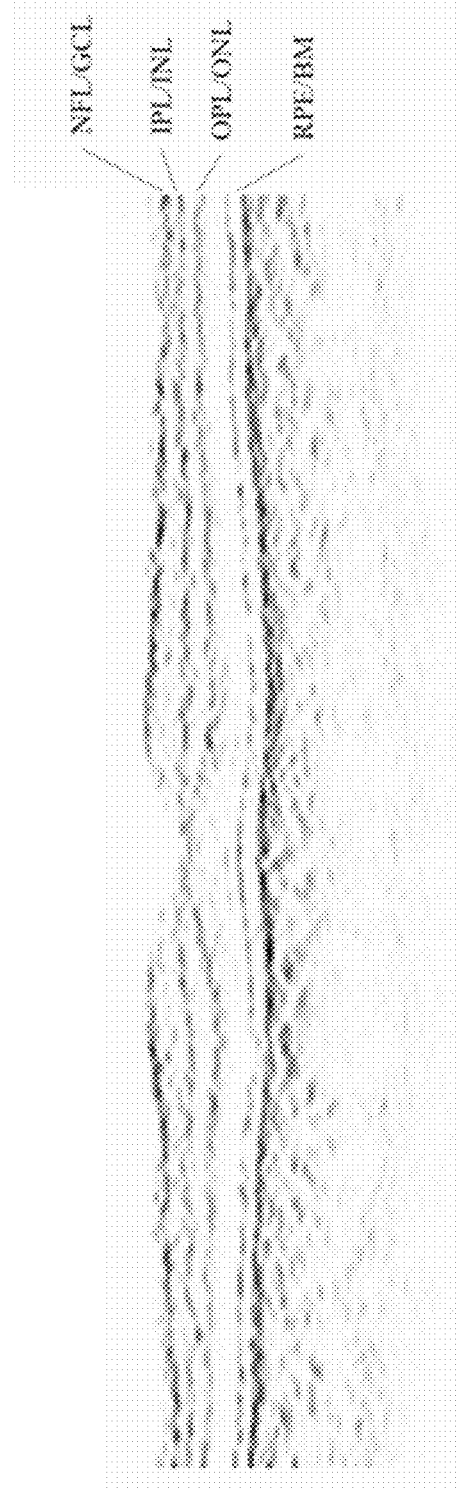

From each gradient map $G_A$, the boundaries were retrieved between the vitreous and the inner limiting membrane (ILM), the inner nuclear layer (INL) and the outer plexiform layer (OPL), as well as the upper boundary of the ellipsoid zone (EZ) (. From each gradient map $G_B$, the remaining four boundaries were retrieved, which were between the nerve fiber layer (NFL) and the ganglion cell layer (GCL), between the inner plexiform layer (IPL) and the inner nuclear layer (INL), between the OPL and the outer nuclear layer (ONL), and between the retinal pigment epithelium (RPE) and Bruch's membrane (BM). FIG. 9 illustrates an example of two gradient maps used for layer segmentation. FIG. 9A illustrates an example of gradient map $G_A$, used to segment and estimate Vitreous/ILM, INL/OPL and EZ boundaries. FIG. 9B illustrates an example of gradient map $G_B$ used to segment and estimate NFL/GCL, IPL/INL, OPL/ONL, and RPE/BM boundaries.

1.3 Guidance Point Array

Next, a guidance point array (GPA) was utilized to perform segmentation based on the estimated boundaries. In this Example, array of points was generated for each estimated boundary identified from the gradient maps $G_A$ and $G_B$, indicating the estimated boundary's approximate position based on information extracted from the gradient maps $G_A$ and $G_B$. This GPA can regulate the subsequent bidirectional graph search for the actual layer boundaries.

Figure 10:
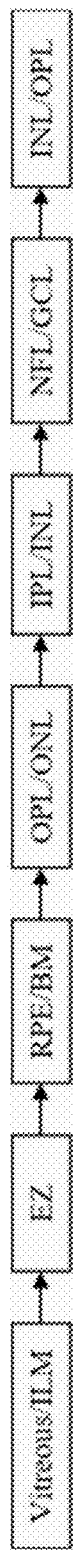
FIG. 10 illustrates the search order of boundaries whose GPAs are identified in a guided bidirectional graph search technique.

FIG. 10 illustrates the search order of boundaries whose GPAs are identified in the guided bidirectional graph search technique. GPAs were generated in a pre-determined order, taking advantage of the characteristics of gradient maps and retinal anatomy to minimize deviations from the correct boundaries. First, the vitreous/ILM and upper EZ boundaries were processed from gradient map $G_A$, as they exhibited the greatest contrast with surrounding tissue. Then, using the EZ layer as the upper boundary, the set of points corresponding to the RPE/BM's GPA was recognized from the $G_B$ gradient map. Subsequently, the upper boundary was fixed at the vitreous/ILM boundary, and $G_B$ was used to sequentially extract the GPA for the OPL/ONL, which had the EZ layer as the lower boundary. Then the GPAs for the IPL/INL and NFL/GCL were extracted, each GPA serving as the lower boundary of the next GPA. Finally, the GPA for the INL/OPL was generated from the gradient map $G_A$ using the IPL/INL and OPL/ONL as upper and lower boundaries, respectively.

The first GPAs to be identified corresponded to the vitreous/ILM and upper EZ boundaries, which were not limited by any reference boundaries. To localize the vitreous/ILM and upper EZ boundaries, speckle noise in the gradient map $G_A$ was reduced by down-sampling the gradient map $G_A$ and the corresponding B-scan by a factor of five to a size of 170×208 pixels. The location of the vitreous/ILM boundary plays a very import role in subsequent operations. For the GPA identification of the vitreous/ILM boundary, a new B-scan (also referred to as an "enhanced B-scan") with enhanced contrast between the vitreous and the ILM was compounded by adding the gradient map $G_A$ to the normalized B-scan. The enhanced B-scan was binarized by thresholding pixels with OCT reflectance values below the average reflectance value, which removed nonzero pixels in the depiction of the vitreous layer in the enhanced B-scan. Then, the first nonzero pixels in each A-line were selected to form the GPA of the vitreous/ILM. For instance, the uppermost nonzero pixels in the binarized enhanced B-scan were defined as the GPA of the vitreous/ILM boundary.

The second GPA to be recognized was the upper EZ boundary. Either the upper EZ boundary or the previously identified vitreous/ILM boundary contain the lowest gradient values in each A-line in the gradient map $G_A$, making the EZ identifiable from the gradient map $G_A$ in view of the previously identified GPA of the vitreous/ILM boundary. Then, the binary image was up-sampled to the original number of pixels, and the 170 GPA points identified were reassigned to the A-lines with indices 5n+1 (n=0 . . . 169).

After the first two GPAs (i.e., the vitreous/ILM and EZ boundary GPAs) were generated from enhanced B-scans, the remaining five were obtained from the corresponding gradient maps, searching one of every five A-lines. The boundary of each remaining GPA could be identified by restricting each search to the corresponding upper and lower boundaries assigned above.

Figures 11A, 11B, 11C:
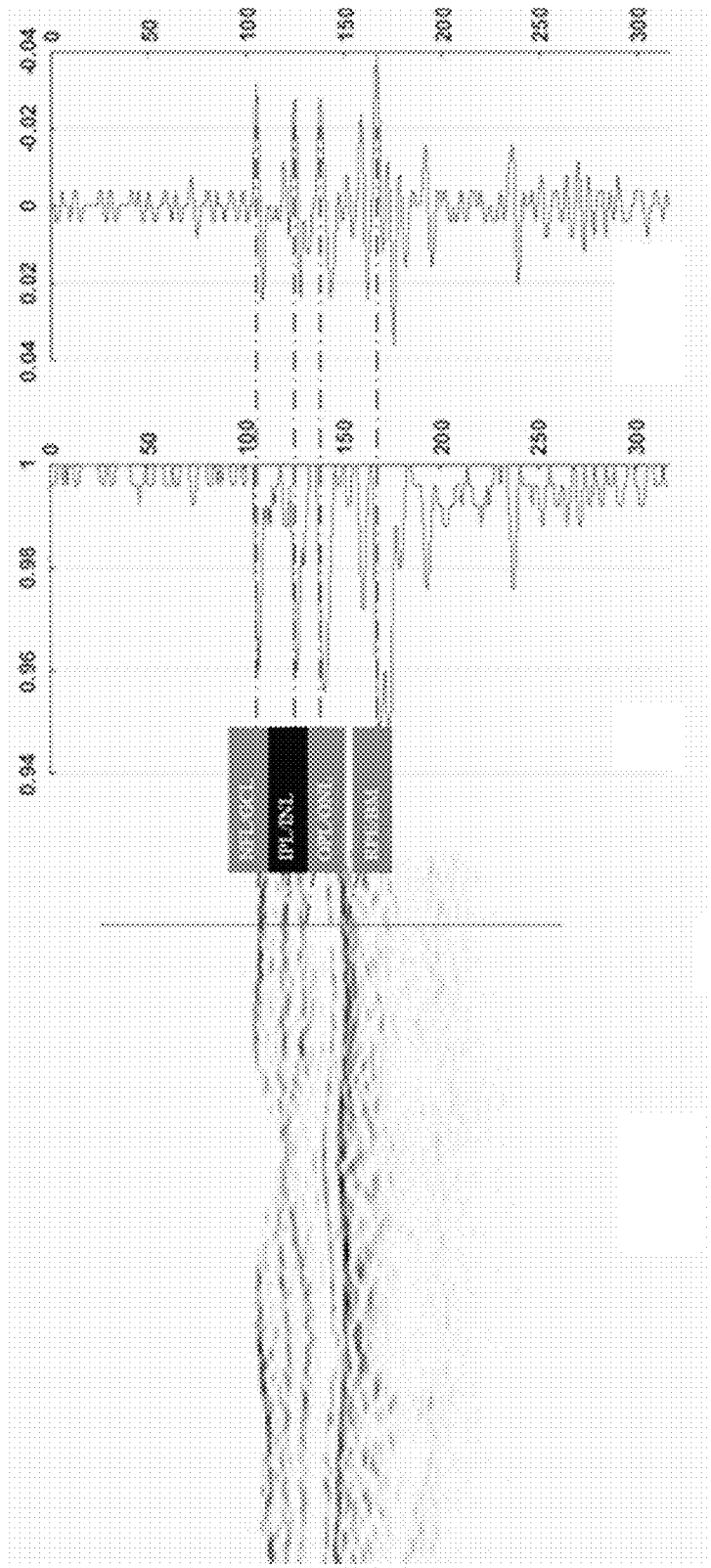

FIG. 11 illustrates an example of search guidance points in an A-scan. Red lines indicate the positions of the NFL/GCL, IPL/INL, OPL/ONL, and RPE/BM in sections (A), (B) and (C). In section (A), the $G_B$ of one B-scan and an A-scan of interest (vertical blue line) are depicted. In section (B), gradient intensities of the A-scan are depicted. In section (C), intensities of (B) after applying the following Equation 5 are depicted.

$$G'_B = G_B * \begin{bmatrix} -1 \\ 0 \\ 1 \end{bmatrix}$$

As shown in section (C) of FIG. 11, these GPAs were first enhanced by a horizontal gradient operator (Equation 5), and the first point with parameter t<−0.02 (where t is the threshold assigned to $G'_B$) was selected for the corresponding GPA, as depicted in section (C) of FIG. 11.

Figures 12A, 12B:
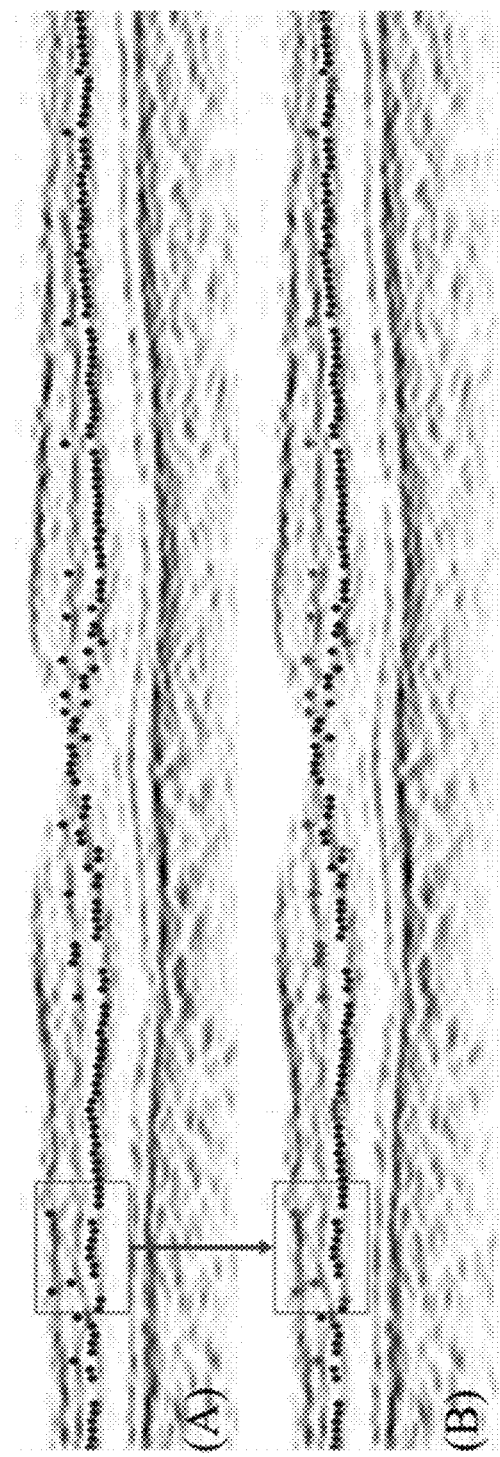
FIGS. 12A and 12B illustrate an example of the removal of unreliable points from an example GPA.

Because of the low contrast and prevalence of noise, points contained in the GPA were occasionally distant from the actual boundary. FIGS. 12A and 12B illustrate an example of the removal of unreliable points from an example GPA. FIG. 12A illustrates GPA points associated with a particular boundary before filtering/removal. FIG. 12B illustrates GPA points after filtering/removal. In FIG. 12B, red asterisks indicate the points removed from the GPA. A mean filter (kernel 1×9) was used on the GPA to remove unreliable points and ensure the accuracy of the operation described below in Section 1.4.

1.4 Guided Bidirectional Graph Search

Figure 13C:
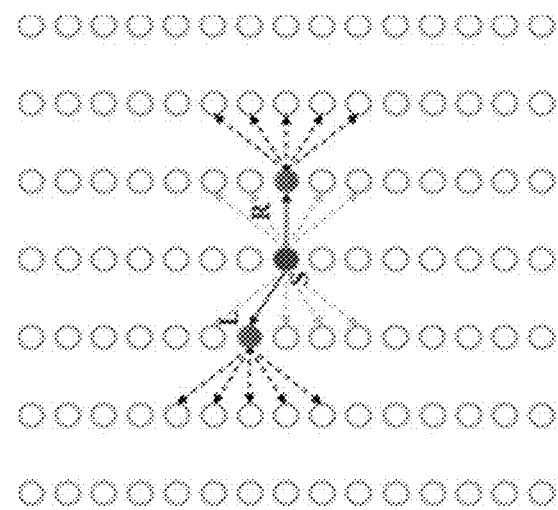
FIGS. 13A to 13C illustrate example implementations of a guided bidirectional graph search.
Figure 13B:
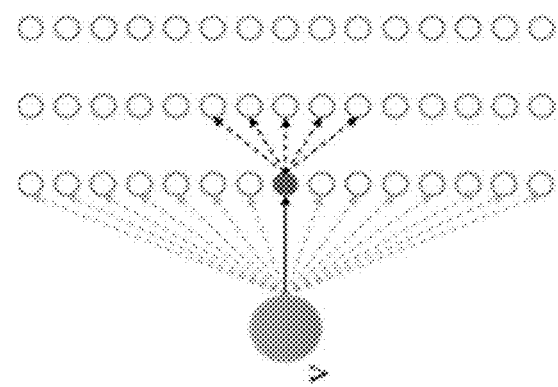
Figure 13A:
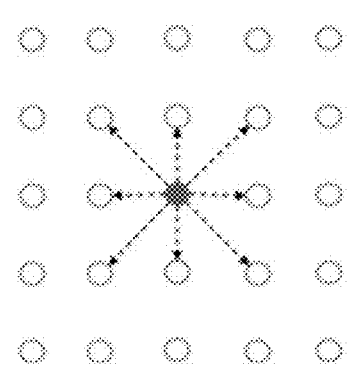

FIGS. 13A to 13C illustrate example implementations of a guided bidirectional graph search utilized in this Example. FIG. 13A illustrates an example of a graph search. FIG. 13B illustrates an example of a directional graph search, in which a virtual start point, V, is located outside of the image. FIG. 13C illustrates an example of a guided bidirectional graph search. When applied to a GPA, a start point, S, depicted in FIG. 13C is contained in the GPA. L and R, in FIG. 13C, represent points searched by a bidirectional graph search technique. After concluding the graph search, a new graph was generated for the next GPA point not included in any of the previous graphs.

Once the GPAs were initially identified after the filtering/removal process, the guided bidirectional graph search technique was implemented for retinal layer segmentation. Referring to FIG. 13C, for any point S, graph points were searched in two directions (left and right). For the next point L (or R), 5 nearby candidate points were appointed in the adjacent A-line (see, e.g., FIGS. 13B and 13C). The candidate point among the nearby candidate points with a minimum gradient was chosen as the next node in the path. Unlike previous directional graph search techniques (e.g., M. Zhang, et al., BIOMEDICAL OPTICS EXPRESS 6(12), 4661 (2015)), a virtual point located outside the image was selected as a starting point. Accordingly, the graph search technique of this Example is configured to cross a collection of points that may or may not fall in the GPA of the boundary under scrutiny.

Figures 14A, 14B, 14C, 14D, 14E:
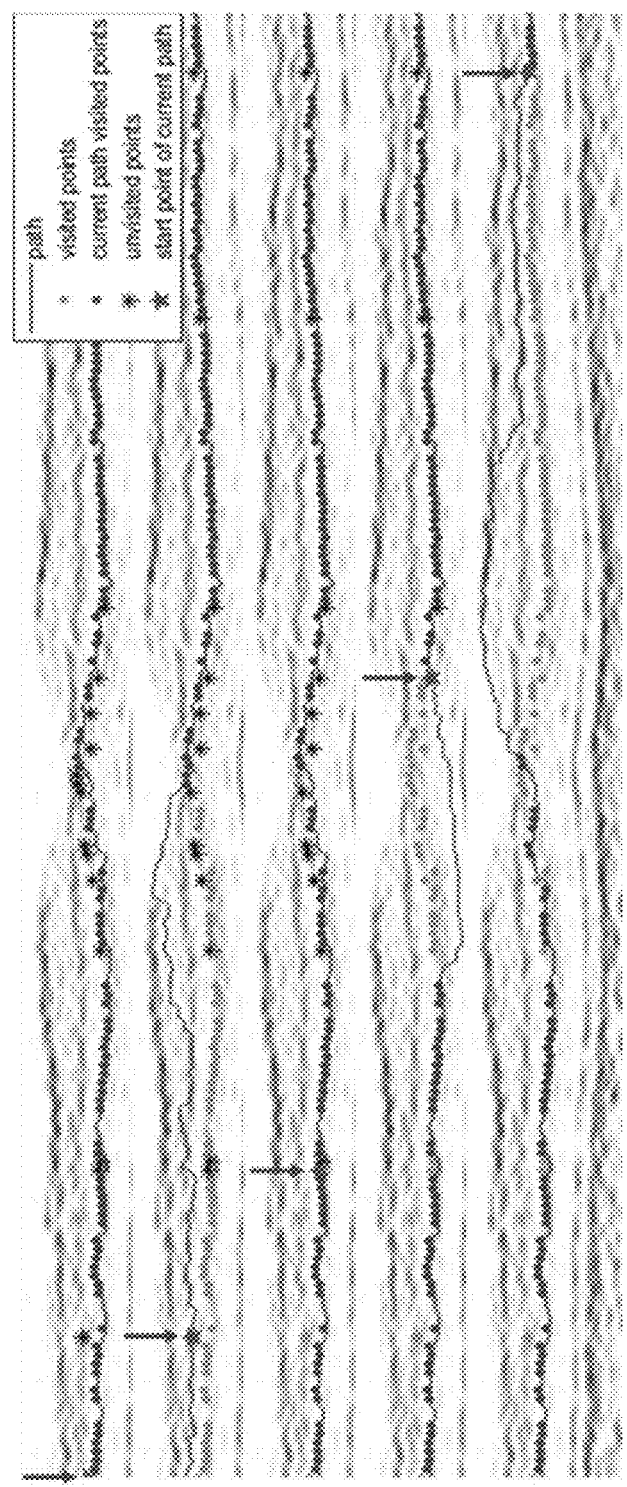
FIGS. 14A to 14E illustrates an example of a guided bidirectional graph search as applied to candidate path identification.

FIGS. 14A to 14E illustrates an example of the guided bidirectional graph search as applied to candidate path identification. Once the GPA was selected, a first graph search was performed starting from a virtual point outside of the image FIG. 14A to generate a first candidate path. GPA points that were located on the first candidate path (red points) and points left out of the first candidate path (blue asterisks) were identified. In addition, a second candidate path was created bi-directionally by graph search, starting from the first GPA point left out of the first candidate path (in FIG. 14B, blue star, red arrow). GPA points omitted from the first candidate path (e.g., blue asterisks) and crossed by the second candidate path did not trigger the start of a future graph search (e.g., these blue asterisks were converted to red points). As shown in FIGS. 14C to 14E, the process was repeated until each one of the GPA points were located in at least one of the candidate paths.

All GPA points crossed by at least one candidate path were dropped from subsequent analysis (see, e.g., FIGS. 14A and 14B). If the graph search generated a first candidate path that diverged from the GPA, another graph search could be performed to generate a second candidate path including at least one point in the GPA that was omitted from the first candidate path. For instance, the guided bidirectional graph search could be started again from the next GPA point that was not contained in any previous graph recognized for the current boundary (see, e.g., FIG. 14B). This process was repeated, generating each time a potentially different graph until all GPA points belonged to one of the graphs representing the candidate paths (see, e.g., FIGS. 14B to 14E). Then, all graphs thus generated were merged by the rationale explained in Section 1.5 below.

Although there were enough points in the GPA to support a point-to-point shortest path search, we preferred the bidirectional graph search to detect the boundary because we observed that some points in the GPA were outside the manually-segmented interfaces. Therefore, the graph of the layer boundary should not be forced to cross all GPA points, and a different boundary detection and merging scheme was necessary.

1.5 Path Merging

Figure 15:
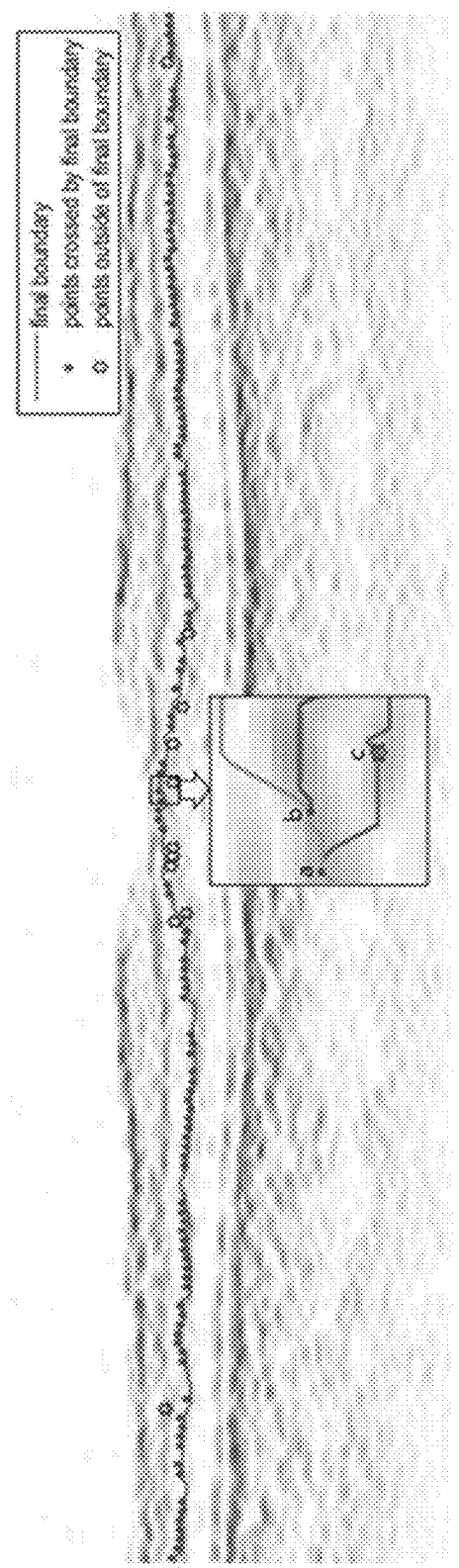
FIG. 15 illustrates an example of a final boundary (red) representing an actual retinal layer boundary after selection of the path with minimum deviation from the GPA points.

FIG. 15 illustrates an example of a final boundary (red) representing the actual boundary after selection of the path with minimum deviation from the GPA points. In this example, the path was selected using the following Equation 6:

$$u = \min_i(|p_i(a) - g(a)| + |p_i(b) - g(b)| + |p_i(c) - g(c)|)$$

where $p_i(x)$ was the value of the i-th candidate path at positon x=a, b, c. g(x) was the GPA evaluated at points x, and the path with the lowest u was chosen between a and b (See FIG. 15).

As illustrated in FIG. 15, two intervals between GPA points a, b, and c were emphasized. Three different paths (similar to those generated in FIG. 14) are represented in light blue, dark blue, and orange color in FIG. 15. According to Equation 6, the pixels crossed by the light blue path were assigned to the final path between points a and b, and the pixels crossed by the dark blue path were assigned to the final path between b and c.

The preceding procedures generated several possible paths for each boundary in a B-scan. To obtain the final boundary, we evaluated the deviation of each candidate path from the corresponding candidate GPA in sections of a B-scan, as depicted in FIG. 15. For example, from an interval bounded by three points of the GPA with indices a, b, and c, we selected the most accurate of all paths (i.e., the closest path to the original candidate GPA derived from the original gradient maps without the graph search) within this interval and assigned it to all A-lines with indices between a and b. To decide the most accurate path within an interval, we designed the evaluation function in Equation 6. Then, the process was repeated for the A-lines in the following interval, i.e., with indices between b and c, etc.

1.6 Segmentation of Capillary Plexuses

Figure 16A:
FIGS. 16A to 16D illustrate example positions of two inner retinal plexuses defined for wide-field OCTA scans (10×8 mm).
Figure 16B:
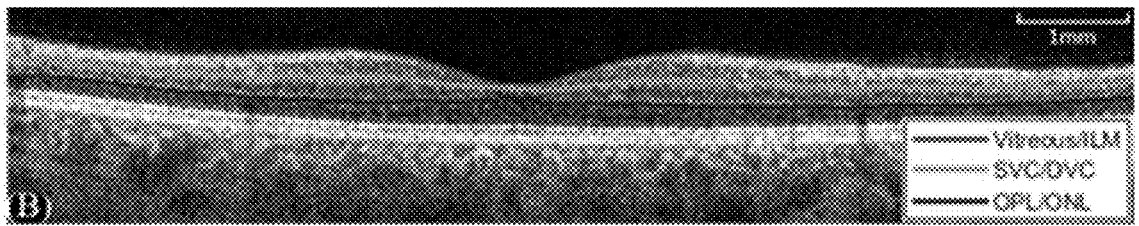
Figure 16C:
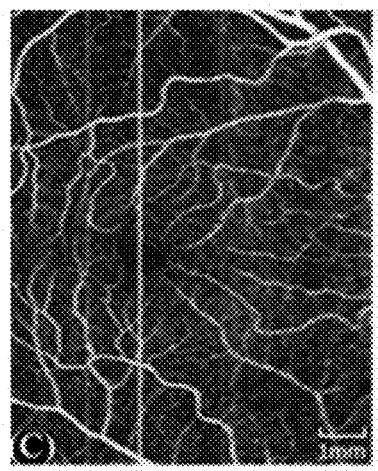
Figure 16D:
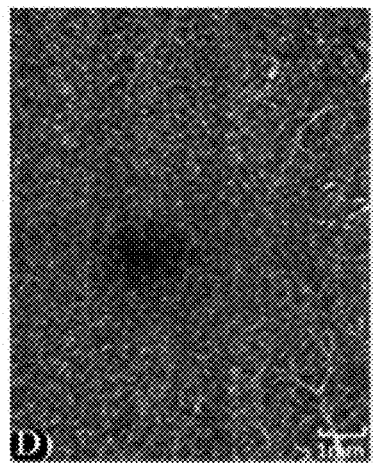

FIGS. 16A to 16D illustrate example positions of two inner retinal plexuses defined for wide-field OCTA scans (10×8 mm). FIG. 16A illustrates a segmented structural OCT scan from a healthy eye. FIG. 16B illustrates upper and lower boundaries of two vascular plexuses in the segmented structural OCT scan. The superficial vascular complex (SVC) was defined between the vitreous/ILM (red line) and the SVC/deep vascular complex (DVC, green line). The SVC/DVC was defined between vitreous/ILM and the IPL/INL (e.g., using techniques described in M. Zhang, et al., BIOMEDICAL OPTICS EXPRESS 6(12), 4661 (2015)), as represented in FIG. 16A. The DVC was defined between the SVC/DVC and OPL/ONL (blue line). FIG. 16C illustrates an en face angiogram of the SVC. The vertical yellow line in FIG. 16C marks the position of the B-scan slice in FIG. 16A. FIG. 16D illustrates the en face angiogram of the DVC.

Two vascular plexuses were extracted from the segmented OCTA volume (depicted in FIGS. 16A and 16B): the SVC (depicted in FIG. 16C) and the DVC (depicted in FIG. 16D). En face angiograms of the capillary plexuses were generated by the maximum projection of OCTA flow signals within the slab.

2. RESULTS 2.1 Study Population

The segmentation method of this example was tested on normal eyes and eyes with glaucoma, diabetic retinopathy, and retinitis pigmentosa (Table 1). For all cases tested, the seven layers were segmented to identify the vitreous/ILM, NFL/GCL, IPL/INL, INL/OPL, OPL/ONL, EZ, and RPE/BM.

TABLE 1

Tested wide-field OCT volumetric data

|  | healthy controls | Glaucoma | Diabetic retinopathy | Retinitis pigmentosa |
|---|---|---|---|---|
| Eyes | 10 | 6 | 7 | 6 |
| Volumetric scans | 10 | 10 | 8 | 9 |

2.2 Segmentation Performance

The GB-GS algorithm was executed in Matlab R2017a on a desktop PC equipped with an Intel® Core™ i7-6700K @4.0 GHz CPU and 32 GB RAM. The average run time of the algorithm was 0.3 seconds per B-scan.

FIG. 17 illustrates retinal segmentation results of the automated segmentation method. FIGS. 17A to 17C illustrate examples of correct segmentation. The red arrows point to positions that were correctly segmented, even though the boundaries were affected by shadows (FIG. 17A) and small cysts (FIGS. 17B and 17C). FIGS. 17D and 17F illustrate examples of incorrect segmentation. The red arrows point indicate the areas where the segmentation failed owing to extremely low contrast (FIG. 17D), retinal neovascularization (FIG. 17E), and a partially separated epiretinal membrane (FIG. 17F).

Figure 17C:
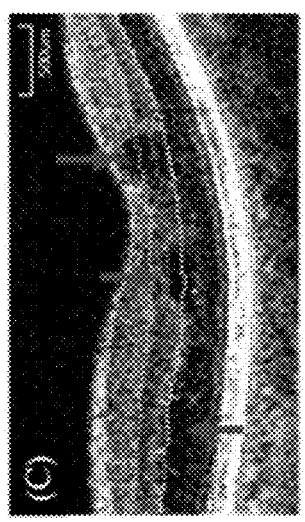
FIGS. 17A to 17F illustrates retinal segmentation results of the automated segmentation technique.
Figure 17F:
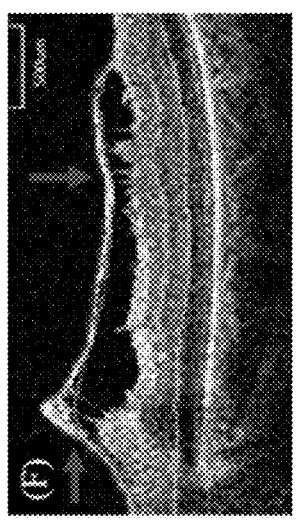
Figure 17B:
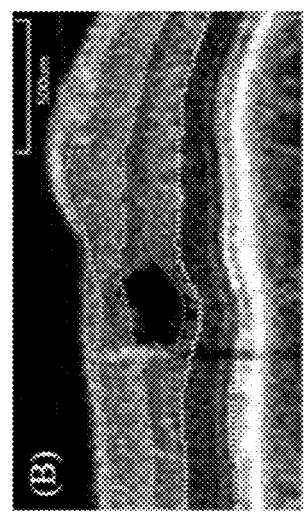
Figure 17E:
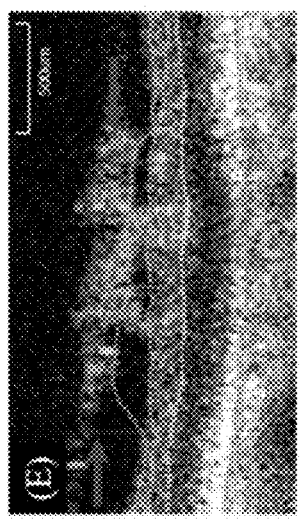
Figure 17A:
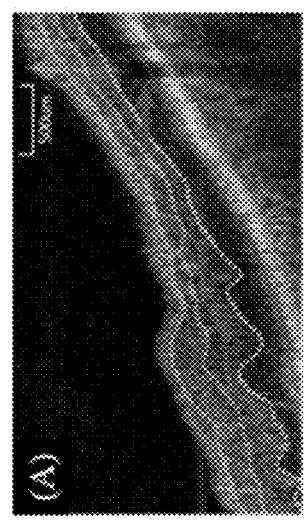
Figure 17D:
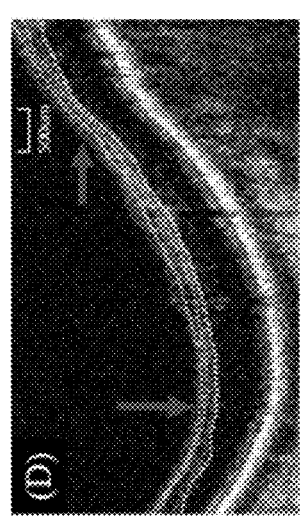

The automatic segmentation method described in this Example correctly segmented retinal layer boundaries, even in the areas of large vessel shadows (FIG. 17A) and small cysts (FIGS. 17B and 17C). Segmentation errors were present in areas of extremely low contrast between layers (FIG. 17D); in areas with retinal neovascularization, which could significantly affect the surface of the ILM (FIG. 17E); and in an area with a partially separated epiretinal membrane (FIG. 17F).

To evaluate segmentation accuracy, the automatic segmentation results were compared with manual segmentation performed by a masked grader. For each eye, 20 B-scans of one volumetric dataset were randomly selected for evaluation. The position of the manual boundary was subtracted from the position of the automatic boundary without any manual corrections in all A-lines under scrutiny, and the segmentation accuracy was determined (Table 2). Subpixel accuracy was present for the four groups, with the most accurate being the vitreous/ILM boundary, which is the one with the highest perceived contrast.

Thanks to the stability and robustness of GB-GS, the automatic segmentation method of this Example can also be used to segment small field of view OCT scans (3×3 and 6×6-mm). To evaluate the performance on small field-of-view OCT scans, 20 volumetric scans acquired by a 70-kHz commercial AngioVue system (RTVue-XR; Optovue, Inc.) were randomly selected (Table 3). The segmentation errors between the automatic segmentation performed by the method of this Example were compared to errors from a previous segmentation method developed by Zhang et al. (M. Zhang, et al., BIOMEDICAL OPTICS EXPRESS 6(12), 4661 (2015)) as well as a segmentation method utilized by the publicly available OCTExplorer software (download from https://www.iibi.uiowa.edu/oct-reference) (B. Antony, et al., BIOMEDICAL OPTICS EXPRESS 2(8), 2403-2416 (2011); M. K. Garvin, et al., IEEE TRANSACTIONS ON MEDICAL IMAGING 28(9), 1436-1447 (2009); K. Li, et al., IEEE TRANSACTIONS ON PATTERN ANALYSIS AND MACHINE INTELLIGENCE 28(1), 119-134 (2006)).

TABLE 3

Tested AngioVue OCT volumetric data

|  | 3 × 3-mm | | 6 × 6-mm | |
|---|---|---|---|---|
| Diagnosis | Diabetic retinopathy | Healthy | Diabetic retinopathy | Healthy |
| Eyes | 5 | 5 | 5 | 5 |
| Volumetric scans | 5 | 5 | 5 | 5 |

31 B-scans from each volumetric scan were selected, for a total of 620 B-scans. For each B-scan, the three methods to segment 7 retinal boundaries, respectively. The segmentation results of the three methods were compared to manual grading (Table 4). As shown in Table 4, the method of this Example is superior (i.e., more closely aligned with manual segmentation) than other two methods on at least five of seven layers.

TABLE 2

Difference in segmentation between manual grading and automated grading for different clinical cases

| Diagnosis | Vitreous/ILM | NFL/GCL | IPL/INL | INL/OPL | OPL/ONL | EZ | RPE/BM |
|---|---|---|---|---|---|---|---|
| Healthy | 0.77 ± 3.58 | 1.21 ± 7.70 | 1.54 ± 9.13 | 1.65 ± 9.02 | 2.09 ± 9.74 | 1.98 ± 9.19 | 1.82 ± 8.69 |
| Glaucoma | 1.10 ± 8.69 | 1.21 ± 7.48 | 1.32 ± 7.43 | 1.32 ± 7.15 | 1.38 ± 7.15 | 2.42 ± 8.80 | 2.53 ± 8.75 |
| Diabetic retinopathy | 0.72 ± 3.25 | 0.88 ± 3.41 | 1.87 ± 6.88 | 2.26 ± 8.20 | 2.70 ± 9.35 | 3.08 ± 9.68 | 2.97 ± 9.35 |
| Retinitis pigmentosa | 1.21 ± 8.09 | 2.70 ± 11.39 | 3.14 ± 11.72 | 3.69 ± 12.54 | 4.46 ± 13.37 | 5.06 ± 13.92 | 5.12 ± 13.64 |

Differences in segmentation between manual grading and automated grading were measured in micron and presented as means ± standard deviations. The digital pixel size in the axial direction was 5.5 μm.

TABLE 4

Differences in segmentation between segmentation techniques and manual grading for different size of view field OCT scans

| | | Vitreous/ILM | NFL/GCL | IPL/INL | INL/OPL | OPL/ONL | EZ | RPE/BM |
|---|---|---|---|---|---|---|---|---|
| 3 × 3-mm | OCTExplorer | 9.83 ± 2.75 | 15.71 ± 16.38 | 14.64 ± 12.04 | 15.59 ± 8.44 | 11.63 ± 10.29 | 3.89 ± 5.62 | 11.82 ± 4.73 |
| | Zhang et al | 3.20 ± 2.50 | 7.45 ± 6.30 | 8.09 ± 7.58 | 6.31 ± 7.33 | 7.69 ± 8.41 | 2.95 ± 2.61 | 4.70 ± 3.31 |
| | Example Method | 3.04 ± 0.48 | 5.70 ± 7.19 | 6.20 ± 7.45 | 4.28 ± 4.44 | 4.09 ± 4.12 | 3.32 ± 1.76 | 5.61 ± 3.99 |
| 6 × 6-mm | OCTExplorer | 9.66 ± 3.14 | 13.08 ± 10.79 | 11.13 ± 9.35 | 14.11 ± 7.77 | 10.18 ± 7.29 | 4.31 ± 4.47 | 12.52 ± 5.11 |
| | Zhang et al | 3.58 ± 2.93 | 11.94 ± 17.97 | 9.07 ± 12.50 | 6.15 ± 8.16 | 7.55 ± 10.52 | 3.61 ± 3.82 | 6.03 ± 4.81 |
| | Example Method | 3.11 ± 1.37 | 6.05 ± 11.81 | 6.65 ± 11.65 | 5.85 ± 11.03 | 4.83 ± 8.75 | 4.80 ± 9.20 | 5.79 ± 8.71 |

Differences in segmentation between manual grading and automated grading were measured in micron and presented as means ± standard deviations. The digital pixel size in the axial direction was 3 μm. The best performance on each layer was bolded.

2.3 Clinical Applications

To evaluate the benefits of the automated segmentation method of this Example in the computation of clinically useful parameters, the method was applied to the detection of the nonperfusion area in one eye with DR. Capillary nonperfusion is an important feature of DR (Early Treatment Diabetic Retinopathy Study Research Group, OPHTHALMOLOGY 98(5), 741-756 (1991); M. S. Ip, et al., OPHTHALMOLOGY 122(2), 367-374 (2015)), and quantification of DR may be an important biomarker of disease progression. In particular, the larger scanning area of wide-field OCTA can improve the sensitivity of this metric for early stages of the disease because the manifestations of capillary dropout in DR begin in the peripheral retina rather than the central macula.

Figure 18A:
FIGS. 18A to 18E illustrates example segmentation results from a representative diabetic retinopathy case.
Figure 18E:
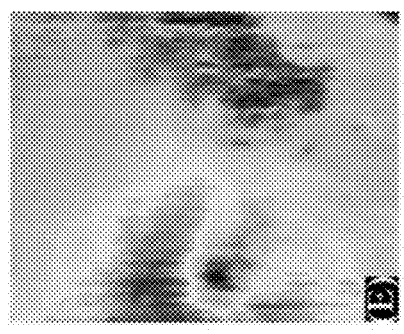
Figure 18D:
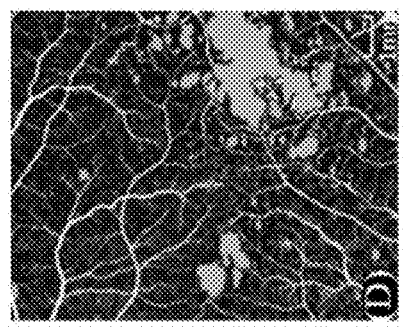
Figure 18C:
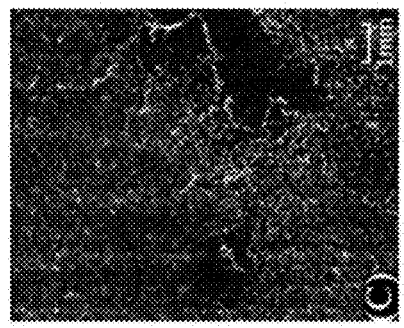
Figure 18B:
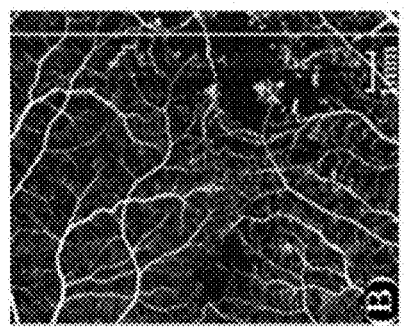

FIGS. 18A to 18E illustrates example segmentation results from a representative diabetic retinopathy case. FIG. 18A illustrates an example of the segmentation of layer boundaries. FIG. 18B illustrates an example of the en face angiogram of the superficial vascular complex. The yellow line in FIG. 18B marks the position of the B-scan slice in FIG. 18A. FIG. 18C illustrates an example of the en face angiogram of the deep vascular complex. FIG. 18D illustrates an example of the nonperfusion area in the superficial vascular complex angiogram. FIG. 18E illustrates an example of a retinal thickness map between vitreous/ILM and RPE/BM.

Using the automated segmentation method of this Example, each layer on a structural OCT B-scan was segmented (see FIG. 18A). The en face angiogram of the SVC and DVC flow were generated (see FIGS. 18B and 18C), and a slab subtraction technique (e.g., as described in Y. Jia, et al., PROCEEDINGS OF THE NATIONAL ACADEMY OF SCIENCES 112(18), E2395-E2402 (2015); Y. Jia, et al., OPHTHALMOLOGY 121(7), 1435-1444 (2014); L. Liu, et al., BIOMEDICAL OPTICS EXPRESS 6(9), 3564 (2015)) was applied to reduce the prevalence of projection artifacts in the DVC. Then, a nonperfusion map (see FIG. 18D) was generated using an automated technique developed previously (see, e.g., Y. Jia, et al., PROCEEDINGS OF THE NATIONAL ACADEMY OF SCIENCES 112(18), E2395-E2402 (2015); Y. Jia, et al., OPHTHALMOLOGY 121(7), 1435-1444 (2014)). The resulting images demonstrated areas of capillary nonperfusion over 7.04 mm² that were specific to individual plexuses (FIGS. 18B and 18C), allowing plexus-specific detection of nonperfusion in OCTA.

Figure 19:
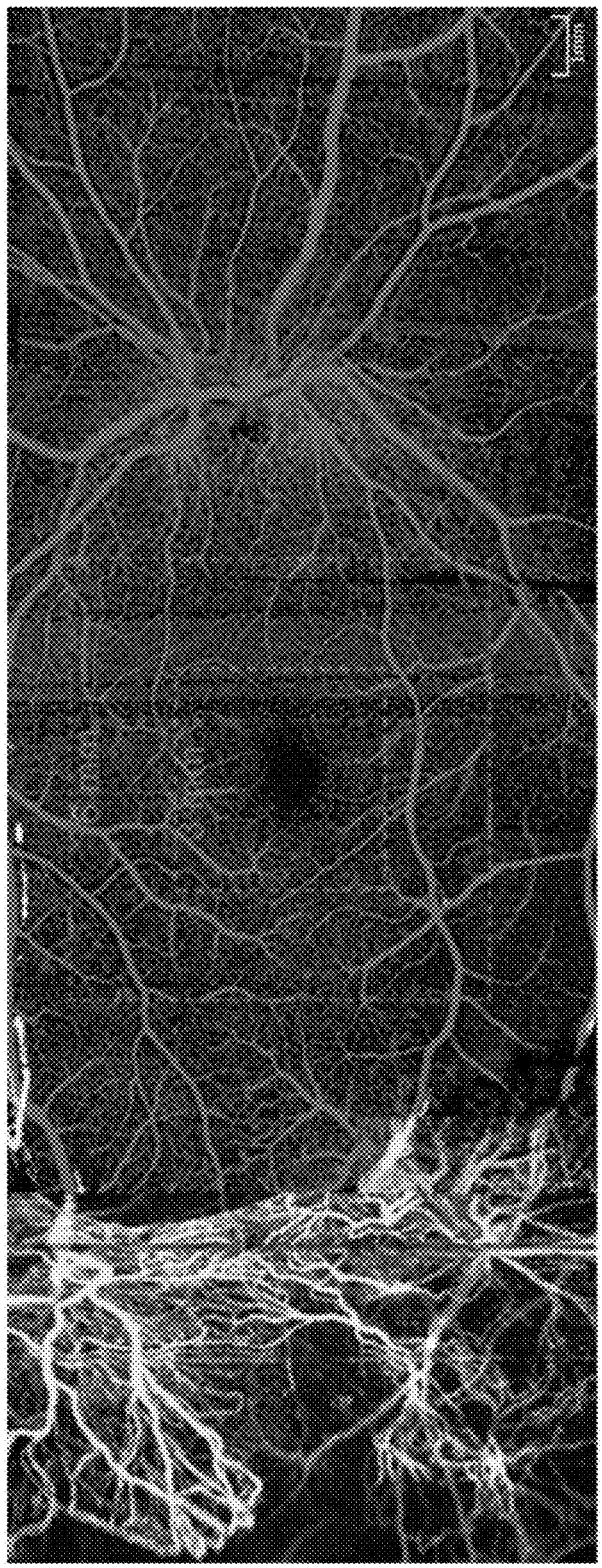
FIG. 19 illustrates an example of wide-field OCTA of a patient with proliferative diabetic retinopathy.

FIG. 19 illustrates an example of wide-field OCTA of a patient with proliferative diabetic retinopathy. A large area of neovascularization (yellow) temporal to the macula was present. The image illustrated in FIG. 19 was montaged from four 10×8-mm scans. The total size of the portion of the patient's eye depicted in FIG. 19 is 10×25 mm. The traditional 3×3- and 6×6-mm commercial OCTA images at the central macular area are indicated by dashed squares respectively. Unlike the fluorescein angiograms, OCTA demonstrates the neovascularization clearly without leakage and allows for quantification.

Another possible use of wide-field OCTA is identification of neovascularization in DR eyes. A 10×25-mm wide-field OCTA, produced by montaging four scans, demonstrates a large area of neovascularization temporal to the macula (FIG. 19). Because wide-field-OCTA visualizes the neovascularization clearly without leakage, quantification of neovascularization is possible, allowing objective monitoring of treatment response.

3. DISCUSSION

In this Example, an automated segmentation method demonstrated an improvement over a previous graph search retinal layer segmentation technique and OCTExplorer technique to achieve a more accurate delineation of the seven layer boundaries imaged by wide-field OCT scanning. The method was able to segment both healthy and diseased retinas, including hypo-reflective regions affected by vascular shadows and retinal cysts.

One example advantage of the automatic segmentation described herein is the ability to accurately segment retinal layers over a large scanning area. Traditional OCTA had been restricted from its inception to narrow fields of view, i.e., 3×3, 4.5×4.5, and 6×6-mm, which are still standard in commercial machines. Wide-field OCTA is a natural evolution of this technology, compelled by the clinical demand for better visualization of the peripheral retina. Stitching many images by registration techniques is an alternative to generate retinal angiograms of larger size, and it is inherently better to montage a few wide-field scans (e.g., 10×6-mm) than numerous narrow-field scans (e.g., 6×6-mm). For instance, the angiogram represented in FIG. 19 was generated by montaging of four 10×8-mm scans, whereas at least ten 6×6-mm scans would be needed to represent the same area. However, the advantage of wide-field scanning comes at the expense of more challenging segmentation across ultra-wide B-scans. Our method based on GB-GS not only can handle the macular area, but also can accurately segment the optic disc region and peripheral retinal region.

Recently, segmentation of retinal layers and pathological structures has also been accomplished by alternative supervised machine learning methods such as deep learning (L. Fang, et al., BIOMEDICAL OPTICS EXPRESS 8(5), 2732-2744 (2017); A. G. Roy, et al., BIOMEDICAL OPTICS EXPRESS 8(8), 3627-3642 (2017)). An advantage of the guided graph search method of this Example is that unlike deep learning solutions, the method does not need a large, annotated dataset to be used for network training, and hence the method is suitable for small studies, for data acquired by lab-built prototype devices, and for diseases in which even manual segmentation of boundaries is uncertain and could introduce confusion during training. Moreover, the machine learning methods reported previously only generated probability maps and still needed a post-processing step (e.g., graph search or conditional random fields) to generate sharp boundaries. In contrast, the results of this Example show that it is generalizable to different retinal pathologies. This method is superior to previous graph search solutions in that it considers the laminar structure of the retina and performs the search in two directions, relying on the GPA to prevent graph deviations from the anatomically connected boundaries. Finally, the method of this Example performs segmentation faster than machine learning alternatives owing to the lower computational requirements.

4. CONCLUSIONS

This Example provides a novel automatic segmentation method, which can be used to find the boundaries of seven retinal layer boundaries in wide-field OCTA images. This method showed sub-pixel accuracy in both normal and diseased eyes. The extraction of thin slab boundaries over a large area has great potential for use in the improved diagnosis and progression assessment of diseases. This is especially true for diseases that begin from the peripheral retina and affect large areas, such as DR and inherited retinal diseases, where evaluation by OCTA was limited in the past to a small field of view.

The environments and individual elements described herein may of course include many other logical, programmatic, and physical components, of which those shown in the accompanying figures are merely examples that are related to the discussion herein.

Other architectures may be used to implement the described functionality and are intended to be within the scope of this disclosure. Furthermore, although specific distributions of responsibilities are defined above for purposes of discussion, the various functions and responsibilities might be distributed and divided in different ways, depending on circumstances.

Furthermore, although the subject matter has been described in language specific to structural features and/or methodological acts, it is to be understood that the subject matter defined in the appended claims is not necessarily limited to the specific features or acts described. Rather, the specific features and acts are disclosed as exemplary forms of implementing the claims.

As will be understood by one of ordinary skill in the art, each embodiment disclosed herein can comprise, consist essentially of, or consist of its particular stated element(s), step(s), ingredient(s), and/or component(s). Thus, the terms "include" or "including" should be interpreted to recite: "comprise, consist of, or consist essentially of." The transition term "comprise" or "comprises" means includes, but is not limited to, and allows for the inclusion of unspecified elements, steps, ingredients, or components, even in major amounts. The transitional phrase "consisting of" excludes any element, step, ingredient or component not specified. The transition phrase "consisting essentially of" limits the scope of the embodiment to the specified elements, steps, ingredients or components and to those that do not materially affect the embodiments. In the current context, a material affect includes accurately identifying position(s) of at least one retinal layer boundary within 0.1 mm.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. When further clarity is required, the term "about" has the meaning reasonably ascribed to it by a person skilled in the art when used in conjunction with a stated numerical value or range, i.e. denoting somewhat more or somewhat less than the stated value or range, to within a range of ±20% of the stated value; ±19% of the stated value; ±18% of the stated value; ±17% of the stated value; ±16% of the stated value; ±15% of the stated value; ±14% of the stated value; ±13% of the stated value; ±12% of the stated value; ±11% of the stated value; ±10% of the stated value; ±9% of the stated value; ±8% of the stated value; ±7% of the stated value; ±6% of the stated value; ±5% of the stated value; ±4% of the stated value; ±3% of the stated value; ±2% of the stated value; or ±1% of the stated value.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventors expect skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents, printed publications, journal articles and other written text throughout this specification (referenced materials herein). Each of the referenced materials are individually incorporated herein by reference in their entirety for their referenced teaching.

It is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

The particulars shown herein are by way of example and for purposes of illustrative discussion of the preferred embodiments of the present invention only and are presented in the cause of providing what is believed to be the most useful and readily understood description of the principles and conceptual aspects of various embodiments of the invention. In this regard, no attempt is made to show structural details of the invention in more detail than is necessary for the fundamental understanding of the invention, the description taken with the drawings and/or examples making apparent to those skilled in the art how the several forms of the invention may be embodied in practice.

Explicit definitions and explanations used in the present disclosure are meant and intended to be controlling in any future construction unless clearly and unambiguously modified in the following examples or when application of the meaning renders any construction meaningless or essentially meaningless. In cases where the construction of the term would render it meaningless or essentially meaningless, the definition should be taken from Webster's Dictionary, 3rd Edition or a dictionary known to those of ordinary skill in the art, such as the Oxford Dictionary of Biochemistry and Molecular Biology (Ed. Anthony Smith, Oxford University Press, Oxford, 2004).

What is claimed is:

1. A system, comprising:
    at least one processor; and
    memory storing instructions that, when executed by the at least one processor, cause the at least one processor to perform operations comprising:
        identifying a reflectance image of the retina of a subject;
        generating a gradient map of the reflectance image, the gradient map representing dark-to-light or light-to-dark reflectance differentials between adjacent pixel pairs in the reflectance image;
        generating a guidance point array corresponding to a retinal layer boundary depicted in the reflectance image using the gradient map;
        generating multiple candidate paths estimating the retinal layer boundary in the reflectance image by performing a guided bidirectional graph search on the reflectance image using the guidance point array;
        identifying the retinal layer boundary by merging two or more of the multiple candidate paths; and
        causing an electronic device to output the retinal layer boundary.

2. The system of claim 1, wherein the operations further comprise:
    generating an avascular map of the retina of the subject using the retinal layer boundary, a reflectance intensity map of the retina, and an optical coherence tomography angiography (OCTA) image of the retina, the avascular map indicating at least one area of nonperfusion depicted in the OCTA image; and
    causing the electronic device to output the avascular map.

3. The system of claim 2, wherein causing the electronic device to output the retinal layer boundary comprises causing the electronic device to display the reflectance image and the retinal layer boundary, and
    wherein causing the electronic device to output the avascular map comprises causing the electronic device to display the OCTA image overlaid with the avascular map.

4. The system of claim 1, further comprising:
    an imaging device configured to generate the reflectance image by scanning the retina of the subject.

5. The system of claim 1, wherein the guidance point array corresponds to a first boundary between a vitreous of the retina and an inner limiting membrane (ILM) of the retina, a second boundary between an inner nuclear layer (INL) of the retina and an outer plexiform layer (OPL) of the retina, a third boundary between an upper boundary of an ellipsoid zone (EZ) of the retina, a fourth boundary between a nerve fiber layer (NFL) of the retina and a ganglion cell layer (GCL) of the retina, a fifth boundary between an inner plexiform layer (IPL) of the retina and the INL, a sixth boundary between the OPL and an outer nuclear layer (ONL) of the retina, or a seventh boundary between a retinal pigment epithelium (RPE) of the retina and a Bruch's membrane (BM) of the retina.

6. The system of claim 1, wherein the guidance point array is a first guidance point array and the retinal layer boundary is a first retinal layer boundary,
    wherein the operations further comprise generating a second guidance point array corresponding to a second retinal layer boundary of the retina, and
    wherein generating the first guidance point array comprises searching for the first guidance point array in a portion of the gradient map that is bounded by a second guidance point array corresponding to a second retinal layer boundary of the retina.

7. The system of claim 1, wherein the reflectance image comprises a wide-field B-scan of the retina with a field of view that is at least as wide as 6 millimeters.

8. The system of claim 1, wherein generating the multiple candidate paths comprises:
    selecting a first pixel in the reflectance image corresponding to a first point in the guidance point array;
    identifying a first A-line in the reflectance image comprising the first pixel;
    identifying second pixels in the reflectance image comprised in a second A-line that is adjacent to the first A-line;
    determining differences between a first intensity value of the first pixel and second intensity values of the second pixels;

selecting, among the second pixels, a third pixel corresponding to a minimum difference among the differences; and
defining a particular candidate path among the multiple candidate paths to comprise a position of the first pixel and a position of the third pixel.

9. The system of claim 1, the gradient map being a first gradient map representing dark-to-light reflectance transitions in the reflectance image, the guidance point array being a first guidance point array corresponding to a first boundary between a vitreous and inner limiting membrane (ILM) of the retina, the system further comprising:
an optical coherence tomography (OCT) imaging device configured to generate the reflectance image,
wherein the electronic device comprises an output device,
wherein the system comprises a medical imaging system, and
wherein the operations further comprise:
generating a second gradient map of the reflectance image, the second gradient map representing light-to-dark reflectance transitions in the reflectance image;
generating a second guidance point array corresponding to a second boundary that is an upper boundary of an ellipsoid zone (EZ) of the retina based on the first gradient map and the first guidance point array;
generating a third guidance point array corresponding to a third boundary between a retinal pigment epithelium (RPE) and a Bruch's membrane (BM) of the retina based on the second gradient map and the second guidance point array;
generating a fourth guidance point array corresponding to a fourth boundary between an outer plexiform layer (OPL) and an outer nuclear layer (ONL) of the retina based on the second gradient map and the third guidance point array;
generating a fifth guidance point array corresponding to a fifth boundary between an inner plexiform layer (IPL) and an inner nuclear layer (INL) of the retina based on the second gradient map and the fourth guidance point array;
generating a sixth guidance point array corresponding to a sixth boundary between a nerve fiber layer (NFL) and a ganglion cell layer (GCL) of the retina based on the second gradient map and the fifth guidance point array;
generating a seventh guidance point array corresponding to a seventh boundary between the INL and the OPL of the retina based on first gradient map and the fourth and fifth guidance point arrays;
identifying the second to seventh boundaries by performing bidirectional graph searches of the reflectance image based on the second to seventh guidance point arrays; and
causing the output device to output the reflectance image and indications of the first to seventh boundaries.

10. The system of claim 9, wherein the OCT imaging device is further configured to generate a reflectance intensity map of the retina and an optical coherence tomography angiography (OCTA) image of the retina, and
wherein the operations further comprise:
generating an avascular map of the retina based on the first to seventh boundaries, the reflectance intensity map, and the OCTA image, the avascular map indicating at least one area of nonperfusion depicted in the OCTA image; and
causing the output device to output the avascular map.

11. The system of claim 9, wherein the reflectance image comprises a B-scan of the retina with a field of view that is greater than 6 millimeters.

12. A method, comprising:
identifying a reflectance image of the retina of a subject;
generating a gradient map of the reflectance image, the gradient map representing dark-to-light or light-to-dark reflectance differentials between adjacent pixel pairs in the reflectance image;
generating a guidance point array corresponding to a retinal layer boundary depicted in the reflectance image using the gradient map;
generating multiple candidate paths estimating the retinal layer boundary in the reflectance image by performing a guided bidirectional graph search on the reflectance image using the guidance point array;
identifying the retinal layer boundary by merging two or more of the multiple candidate paths; and
causing an electronic device to output the retinal layer boundary.

13. The method of claim 12, further comprising:
generating an avascular map of the retina of the subject using the retinal layer boundary, a reflectance intensity map of the retina, and an optical coherence tomography angiography (OCTA) image of the retina, the avascular map indicating at least one area of nonperfusion depicted in the OCTA image; and
causing the electronic device to output the avascular map.

14. The method of claim 12, wherein causing the electronic device to output the retinal layer boundary comprises causing the electronic device to display the reflectance image and the retinal layer boundary, and
wherein causing the electronic device to output the avascular map comprises causing the electronic device to display the OCTA image overlaid with the avascular map.

15. The method of claim 12, wherein the guidance point array is a first guidance point array and the retinal layer boundary is a first retinal layer boundary,
wherein the method further comprises generating a second guidance point array corresponding to a second retinal layer boundary of the retina, and
wherein generating the first guidance point array comprises searching for the first guidance point array in a portion of the gradient map that is bounded by a second guidance point array corresponding to a second retinal layer boundary of the retina.

16. The method of claim 12, wherein the reflectance image comprises a wide-field B-scan of the retina with a field of view that is at least as wide as 6 millimeters.

17. The method of claim 12, wherein generating the multiple candidate paths comprises:
selecting a first pixel in the reflectance image corresponding to a first point in the guidance point array;
identifying a first A-line in the reflectance image comprising the first pixel;
identifying second pixels in the reflectance image comprised in a second A-line that is adjacent to the first A-line;
determining differences between a first intensity value of the first pixel and second intensity values of the second pixels;
selecting, among the second pixels, a third pixel corresponding to a minimum difference among the differences; and
defining a particular candidate path among the multiple candidate paths to comprise a position of the first pixel and a position of the third pixel.

18. The method of claim 12, wherein the gradient map represents dark-to-light reflectance differentials and is generated using the following equation:

$$G(x, z) = I(x, z) - I(x, z-1); x = 1, 2, \ldots, N; z = 1, 2, \ldots, M$$

$$G_A(x, z) = \begin{cases} 1 - G(x, z), & G(x, z) > 0 \\ 1, & \text{otherwise} \end{cases},$$

wherein I(x,z) is a reflectance value of the reflectance image at position (x ,z), M is the length of A-scans in the reflectance image in pixels, N is the width of the reflectance image in pixels, and $G_A(x, z)$ is a value of the gradient map at position (x, z), and wherein the guidance point array corresponds to a first boundary between a vitreous of the retina and an inner limiting membrane (ILM) of the retina, a second boundary between an inner nuclear layer (INL) of the retina and an outer plexiform layer (OPL) of the retina, or a third boundary between the INL and an outer plexiform layer (OPL) of the retina.

19. The method of claim 12, wherein the gradient map represents light-to-dark reflectance differentials and is generated using the following equation:

$$G(x, z) = I(x, z) - I(x, z-1); x = 1, 2, \ldots, N; z = 1, 2, \ldots, M$$

$$G_B(x, z) = \begin{cases} 1 - |G(x, z)|, & G(x, z) < 0 \\ 1, & \text{otherwise} \end{cases},$$

wherein I(x,z) is a reflectance value of the reflectance image at position (x ,z), M is the length of A-scans in the reflectance image in pixels, N is the width of the reflectance image in pixels, and GB(x, z) is a value of the gradient map at position (x, z), and wherein the guidance point array corresponds to a first boundary between a nerve fiber layer (NFL) of the retina and a ganglion cell layer (GCL) of the retina, a second boundary between an inner plexiform layer (IPL) of the retina and an inner nuclear layer (INL) of the retina, a third boundary between the an outer plexiform layer (OPL) of the retina and an outer nuclear layer (ONL) of the retina, or a fourth boundary between a retinal pigment epithelium (RPE) of the retina and a Bruch's membrane (BM) of the retina.

20. The method of claim 12, wherein identifying the retinal layer boundary by merging the two or more multiple candidate paths comprises:
identifying first segments of the multiple paths that each extend between first and second points;
identifying at least one A-line between the first and second points;
determining distances between a third point in the guidance point array and the at least one A-line and fourth points in the first segments and the at least one A-line;
determining, based on the distances, a particular first segment among the first segments that is closest to the guidance point array; and
defining the retinal layer boundary to comprise the particular first segment.

\* \* \* \* \*